US007910372B2

(12) United States Patent
Ishihama

(10) Patent No.: US 7,910,372 B2
(45) Date of Patent: Mar. 22, 2011

(54) ABSOLUTE QUANTITATION OF PROTEIN CONTENTS BASED ON EXPONENTIALLY MODIFIED PROTEIN ABUNDANCE INDEX BY MASS SPECTROMETRY

(75) Inventor: Yasushi Ishihama, Tsuruoka (JP)

(73) Assignee: EISAI R&D Management Co., Ltd., Tokyo (JP)

( * ) Notice: Subject to any disclaimer, the term of this patent is extended or adjusted under 35 U.S.C. 154(b) by 1079 days.

(21) Appl. No.: 11/658,592

(22) PCT Filed: Jul. 4, 2005

(86) PCT No.: PCT/JP2005/012705
§ 371 (c)(1),
(2), (4) Date: Jan. 26, 2007

(87) PCT Pub. No.: WO2006/011351
PCT Pub. Date: Feb. 2, 2006

(65) Prior Publication Data
US 2008/0319676 A1 Dec. 25, 2008

Related U.S. Application Data

(60) Provisional application No. 60/591,963, filed on Jul. 29, 2004.

(51) Int. Cl.
*G01N 33/00* (2006.01)
*G01N 33/48* (2006.01)
(52) U.S. Cl. ............................................ 436/86; 702/19
(58) Field of Classification Search .................. None
See application file for complete search history.

(56) References Cited

FOREIGN PATENT DOCUMENTS

| WO | WO 02/052259 | 7/2002 |
|---|---|---|
| WO | WO 03/054549 | 7/2003 |
| WO | WO 03/089937 | 10/2003 |

OTHER PUBLICATIONS

Link et al. "Direct analysis of protein complexes using mass spectrometry," Nature Biotechnology 1999, 17, 676-682.*
R. Aebersold, et al.; Mass Spectrometry-Based Proteomics; Nature, vol. 422; Mar. 2003; pp. 198-207.
Y. Oda, et al.; Accurate Quantitation of Protein Expression and Site-Specfic Phosphorylation; Proc. Natl. Acad. Sci USA; vol. 96, Jun. 1999; pp. 6591-6596.
S. Gygi, et al.; Quantitative Analysis of Complex Protein Mixtures Using Isotope-Coded Affinity Tags; Nature Biotechnology; vol. 17; Oct. 1999; pp. 994-999.

(Continued)

*Primary Examiner* — Yelena G Gakh
*Assistant Examiner* — Michelle M Adams
(74) *Attorney, Agent, or Firm* — Morgan, Lewis & Bockius LLP

(57) ABSTRACT

The present inventor has established protein abundance index (PAI, $\pi$) to determine the protein contents in a protein mixture solution using nanoLC-MSMS data. Digested peptides were analyzed by nanoLC-MS/MS and the obtained results were applied to a Mascot protein identification algorism based on tandem mass spectra. For absolute quantitation, PAI was converted to exponentially modified PAI (EMPAI, $m\pi$), which is proportional to protein contents in the protein mixture. EMPAI was successfully applied to comprehensive protein expression analysis and performed a comparison study between gene and protein expression in an HCT116 human cancer cells. Accordingly, the present invention provides a method and a computer program for quantifying the protein contents based on the protein abundance index.

4 Claims, 11 Drawing Sheets

OTHER PUBLICATIONS

Shao-En Ong, et al.; Stable Isotope Labeling by Amino Acids in Cell Culture, Silac, As a Simple and Accurate Approach to Expression Proteomics; Molecular & Cellular Proteomics 1.5; 2002; pp. 376-386.

M.J. Maccoss, et al.; A Correlation Algorithm for the Automated Quantitative Analysis of Shotgun Proteomics Data; Analytical Chemistry; vol. 75, No. 24; Dec. 15, 2003; pp. 6912-6921.

L. Foster, et al.; Unbiased Quantitative Proteomics of Lipid Rafts Reveals High Specificity for Signaling Factors; Proc Natl Acad Sci USA; vol. 100; No. 10; pp. 5813-5818.

B. Blagoev, et al.; A Proteomics Strategy to Elucidate Functional Protein Protein Interactions Applied to EGF Signaling; Nature Biotechnology; vol. 21; Mar. 2003; pp. 315-318.

J. Ranish, et al., The Study of Macromolecular Complexes by Quantitative Proteomics; Nature Genetics; vol. 33; Mar. 2003; pp. 349-355.

W. Schulze, et al.; A Novel Proteomic Screen for Peptide-Protein Interactions; The Journal of Biological Chemistry; vol. 279, No. 11; Mar. 12, 2004; pp. 10756-10764.

Y. Oda, et al.; Quantitative Chemical Proteomics for Identifying Candidate Drug Targets; Analytical Chemistry; vol. 75; No. 9; May 1, 2003; pp. 2159-2165.

J. Barr, et al.; Isotope Dilution-Mass Spectrometric Quantification of Specific Proteins: Model Application With Apolipoprotein A-1; Clinical Chemistry; 42:10; 1996; pp. 1676-1682.

S. Gerber, et al.; Absolute Quantification of Proteins and Phosphoproteins From Cell Lysates by Tandem MS; Proc Natl Acad Sci; vol. 100, No. 12; Jun. 10, 2003; pp. 6940-6945.

J. Havlis, et al.; Absolute Quantification of Proteins in Solutions and in Polyacrylamide Gels by Mass Spectrometry; Analytical Chemistry; vol. 76; No. 11; Jun. 1, 2004; pp. 3029-3036.

R. Corbin, et al.; Toward a Protein Profile of *Escherichia coli*: Comparison to its Transcription Profile; Proc Natl Acad Sci USA; vol. 100; No. 16; Aug. 5, 2003; 9232-9237.

E. Lasonder, et al.; Analysis of the Plasmodium Falciparum Proteome by High-Accuracy Mass Spectrometry; Nature; vol. 419; Oct. 2002; pp. 537-542.

Y. Shen, et al.; High-Efficiency Nanoscale Liquid Chromatography Coupled On-Line With Mass Spectrometry Using Nanoelectrospray Lonization for Proteomics; Analytical Chemistry; vol. 74; No. 16; Aug. 15, 2002; pp. 4235-4249.

J. Rappsilber, et al.; Large-Scale Proteomic Analysis of the Human Spliceosome; Genome Research; 2002; pp. 1231-1245.

Hongbin Liu, et al.; A Model for Random Sampling and Estimation of Relative Protein Abundance in Shotgun Proteomics; Analytical Chemistry; vol. 76; No. 14; Jul. 15, 2004; pp. 4193-4201.

J. S. Anderson, et al.; Proteomic Characterization of the Human Centrosome by Protein Correlation Profiling; Nature; vol. 426; Dec. 2003; pp. 570-574.

J. Rappsilber, et al.; Stop and Go Extraction Tips for Matrix-Assisted Laser Desorption/Lonization, Nanoelectrospray, and LC/MS Sample Pretreatment in Proteomics; Analytical Chemistry; vol. 75, No. 3, Feb. 1, 2003; pp. 663-670.

Y. Ishihama, et al.; Microcolumns With Self-Assembled Particle Frits for Proteomics; Journal of Chromatography A, 979; 2002; pp. 233-239.

J. L. Meek; Prediction of Peptide Retention Times in High-Pressure Liquid Chromatography on the Basis of Amino Acid Composition; Proc Natl Acad Sci USA; vol. 77; No. 3; Mar. 1980; pp. 1632-1636.

Yasuhiro Sakamoto, et al.; Prediction of Peptide Retention Times; Journal of Chromatography; 442; 1988; pp. 69-79.

A. Link, et al.; Direct Analysis of Protein Complexes Using Mass Spectrometry; Nature Biotechnology; vol. 17; Jul. 1999; pp. 676-682.

S. Gygi, et al.; Correlation Between Protein and MRNA Abundance in Yeast; Molecular and Cellular Biology; Mar. 1999; pp. 1720-1730.

W. H. Mager; Control of Ribosomal Protein Gene Expression; Biochimica et Biophysica 949; 1988; pp. 1-15.

E. Lasonder, et al.; Analysis of the Plasmodium Falciparum Proteome by High-Accuracy Mass Spectrometry; Nature; vol. 419; Oct. 3, 2002; pp. 537-542.

Y. Ishihama, et al. "Exponentially modified protein abundance index (emPAI) for estimation of absolute protein amount in proteomics by the number of sequenced peptides per protein." Molecular & Cellular Proteomics, vol. 4, No. 9, Jun. 14, 2005; pp. 1265-1272.

J. Rappsilber, et al; In Proceedings of 51st ASMS Conference on Mass Spectrometry and Allied Topics; Montreal, Quebec, Canada, Jun. 8-12, 2003, Abstract.

K. Tsurugi, Seikagaku; 61(4), (1989), pp. 271-284.

\* cited by examiner

ABSOLUTE QUANTITATION OF PROTEIN CONTENTS BASED ON EXPONENTIALLY MODIFIED PROTEIN ABUNDANCE INDEX BY MASS SPECTROMETRY

This application is a national stage application of PCT International Application No. PCT/JP2005/012705, filed Jul. 4, 2005. This application also claims the benefit of US Provisional Application No. 60/591,963, filed Jul. 29, 2004.

TECHNICAL FIELD

The present invention generally relates to analysis of protein contents by means of mass spectrometry, and more particularly to a method and a computer program for executing quantitation of the protein contents based on protein abundance index by mass spectrometry in proteomics.

BACKGROUND OF ART

Proteomic liquid chromatography-mass spectrometry (hereinafter referred to as "LC-MS") approaches today combined with genome-annotated database allow to identify thousands of proteins from a protein mixture solution [1]. These approaches have been also applied to relative quantitation using stable isotope labeling [2-4]. Recently, not only comprehensive quantitation studies between two states [5,6], but also interaction analysis between protein-protein [7,8], protein-peptides [9] and protein-drug [10] have been extensively reported. So far, however, a comprehensive approach for protein contents in one sample solution has not been established yet. Protein concentrations are one of the most basic and important parameters in quantitative proteomics because the kinetics/dynamics of cellular proteins are described as changes in concentrations of proteins in particular regions. In addition, protein concentrations in a sample can be also used for relative quantitation between two samples even when the difference in concentration is too large to perform isotope-based relative; quantitation. So far, isotope-labeled synthetic peptides were used as internal standards for absolute quantitation of particular proteins of interest [11,12]. This approach would be applicable to comprehensive analysis but the cost of isotope-labeled peptides as well as the difficulty to do quantitative digestion of proteins in gel would cause a problem [13].

Even a single analysis of nanoLC-MS/MS generates a long list of identified proteins easily with the help of database searching, and additional information is extracted from this list with raw data, such as hit ranking in identification, the probability score, the number of identified peptides per protein and ion counts of identified peptides, LC retention times, and so on. Qualitatively, some parameters such as the hit rank, the score and the number of peptides per protein [14] would be a kind of indicators for protein abundance in the analyzed sample. Among them, ion counts of peptides would be the most direct parameter to describe the abundance and were used for protein expression at different states [15]. However, a mass spectrometer as a detector is not so versatile as an absorbance detector in terms of the limited linearity and the ionization suppression effect with background [16]. Therefore, it is required to normalize these parameters to obtain reliable quantitative information. The first approach along this strategy was, as far as the present inventor knows, to use the number of peptides per proteins normalized by theoretical number of peptides, which was named protein abundance index (hereinafter referred to as "PAI"), and was applied to human spliceosome complex analysis [17]. Similar concept was recently reported that the number of peptides or spectra counts in LC/LC-MS/MS analysis were used for relative quantitation [18]. The present inventor also developed normalized ion counts-based approach, where at least three peptides are used to calculate the average ion counts of each protein [19]. This approach has been used for relative quantitation in peptide correlation profiling [20].

DISCLOSURE OF INVENTION

However, the applicability of this approach was limited because it needs three peptides at least to keep the accuracy. Here the present inventor explores the PAI strategy to determine protein abundance from nanoLC-MS/MS experiments.

It is an object of the present invention to provide a method for executing quantitation of protein contents based on an exponentially modified PAI (hereinafter referred as to "EMPAI") in a sample of biological material.

In an embodiment of the present invention, there is also provided a computer program product, for example, a computer readable medium which can be read by a computer and stores a computer program for executing quantitation of protein contents based on the above EMPAI in a sample of biological material.

In another embodiment of the present invention, there is also provided a computer program for executing quantitation of protein contents based on the above EMPAI in a sample of biological material.

In further embodiment of the present invention, there is also provided an analytical apparatus for executing quantitation of protein contents based on the above EMPAI in a sample of biological material.

In order to attain the above object, the present invention provides a method for executing quantitation of protein content in a sample of biological material, said method comprising the steps of: (a) identifying a protein to be quantified by mass spectrometry; (b) measuring the number of observed peptides per the protein ($N_{obsd}$); (c) calculating the number of observable peptides per protein ($N_{obsbl}$); and (d) computing the following equation to obtain EMPAI:

$$EMPAI = 10^{N_{obsd}/N_{obsbl}} - 1.$$

In one preferred aspect of the method according the present invention, the method further comprises calculating protein contents (mol %) based on a value of EMPAI as follows:

$$\text{protein contents (mol \%)} = \frac{EMPAI}{\sum(EMPAI)} \times 100,$$

wherein $\Sigma(EMPAI)$ is the summation of EMPAI values for all identified proteins.

In another preferred aspect of the method according to the present invention, the method further comprises calculating protein contents (weight %) based on a value of EMPAI as follows:

$$\text{protein contents (weight \%)} = \frac{EMPAI \times MW}{\sum(EMPAI \times MW)} \times 100,$$

wherein $\Sigma(EMPAI)$ is the summation of EMPAI values for all identified proteins and MW represents molecular weight of each protein identified.

In further preferred aspect of the method according to the present invention, the mass spectrometry comprises a liquid chromatography-mass spectrometry.

The present invention also provides a computer program product for executing quantitation of protein content in a sample of biological material, said program product comprising: a computer readable storage medium having a computer program stored there on for performing the steps: (a) identifying a protein to be quantified by mass spectrometry; (b) measuring the number of observed peptides per the protein ($N_{obsd}$); (C) calculating the number of observable peptides per protein ($N_{obsbl}$); and (d) computing the following equation to obtain EMPAI $$EMPAI = 10^{Nobsd/Nobsbl} - 1.$$

In one preferred aspect of the computer program product according to the present invention, the program comprises performing of calculating protein contents (mol %) based on a value of EMPAI as follows:

$$\text{protein contents (mol \%)} = \frac{EMPAI}{\sum(EMPAI)} \times 100,$$

wherein Σ(EMPAI) is the summation of EMPAI values for all identified proteins.

In another preferred aspect of the computer program product according to the present invention, the program comprises performing of calculating protein contents (weight %) based on a value of EMPAI as follows:

$$\text{protein contents (weight \%)} = \frac{EMPAI \times \text{MW}}{\sum(EMPAI \times \text{MW})} \times 100,$$

wherein Σ(EMPAI) is the summation of EMPAI values for all identified proteins and MW represents molecular weight of each protein identified.

In further aspect of the computer program product according to the present invention, the product is a computer readable recording medium which can be read by a computer.

The present invention also provides a computer program which executes quantitation of protein content in a sample of biological material, said program comprising performing the steps of: (a) identifying a protein to be quantified by mass spectrometry; (b) measuring the number of observed peptides per the protein ($N_{obsd}$); (c) calculating the number of observable peptides per protein ($N_{obsbl}$); and (d) computing the following equation to obtain EMPAI $$EMPAI = 10^{Nobsd/Nobsbl} - 1.$$

In one aspect of the computer program according to the present invention, the program further comprises performing of calculating protein contents (mol %) based on a value of EMPAI as follows:

$$\text{protein contents (mol \%)} = \frac{EMPAI}{\sum(EMPAI)} \times 100,$$

wherein Σ(EMPAI) is the summation of EMPAI values for all identified proteins.

In another aspect of the computer program according to the present invention, the program further comprises performing of calculating protein contents (weight %) based on a value of EMPAI as follows:

$$\text{protein contents (weight \%)} = \frac{EMPAI \times \text{MW}}{\sum(EMPAI \times \text{MW})} \times 100,$$

wherein Σ(EMPAI) is the summation of EMPAI values for all identified proteins and MW represents molecular weight of each protein identified.

The computer program according to the present invention is characterized in that this program causes the respective steps of the method for quantifying protein content according to the present invention to be performed by a computer. The computer program can also be provided in the form of a storage medium where the program is stored as well as can be supplied via a transmission medium, such as the Internet.

The present invention also provides an analytical apparatus for executing quantification of protein content in a sample of biological material, comprising: identifying means for receiving information as to a mass spectrometric data of proteins obtained by mass spectrometry and identifying a protein to be quantified by the mass spectrometry; measuring means for measuring the number of observed peptides per the protein ($N_{obsd}$); calculating means for calculating the number of observable peptides per protein ($N_{obsbl}$); and computing means for computing the following equation to obtain EMPAI $$EMPAI = 10^{Nobsd/Nobsbl} - 1.$$

In one aspect of the analytical apparatus according to the present invention, the computing means comprises performing of calculating protein contents (mol %) based on a value of EMPAI as follows:

$$\text{protein contents (mol \%)} = \frac{EMPAI}{\sum(EMPAI)} \times 100,$$

wherein Σ(EMPAI) is the summation of EMPAI values for all identified proteins.

In another aspect of the analytical apparatus according to the present invention, the computing means comprises performing of calculating protein contents (weight %) based on a value of EMPAI as follows:

$$\text{protein contents (weight \%)} = \frac{EMPAI \times \text{MW}}{\sum(EMPAI \times \text{MW})} \times 100,$$

wherein Σ(EMPAI) is the summation of EMPAI values for all identified proteins and MW represents molecular weight of each protein identified.

In further aspect of the analytical apparatus according to the present invention, the mass spectrometry comprises a liquid chromatography-mass spectrometry.

An advantage of the present invention is that the scale for absolute protein abundance, namely exponentially modified protein abundance index is established, which can use for absolute quantitation of protein contents in proteomics.

BRIEF DESCRIPTION OF THE DRAWINGS

The above object and features of the present invention will be more apparent from the following description of the preferred embodiments with reference to the accompanying drawings, wherein:

FIG. 5 illustrates dependence of the number of peptides and peak area on the injected amounts of human serum albumin (HSA).

FIG. 6 shows the relationship between protein concentration and different parameters for 47 proteins in neuro2a cells.

FIG. 7 shows the influence of MS measurement conditions on linear relationship between PAI and log [protein].

BEST MODE FOR CARRYING OUT THE INVENTION

The present invention is explained in detail using examples including the method for executing quantitation of the protein contents and the computer program for carrying out the method.

Figure 1:
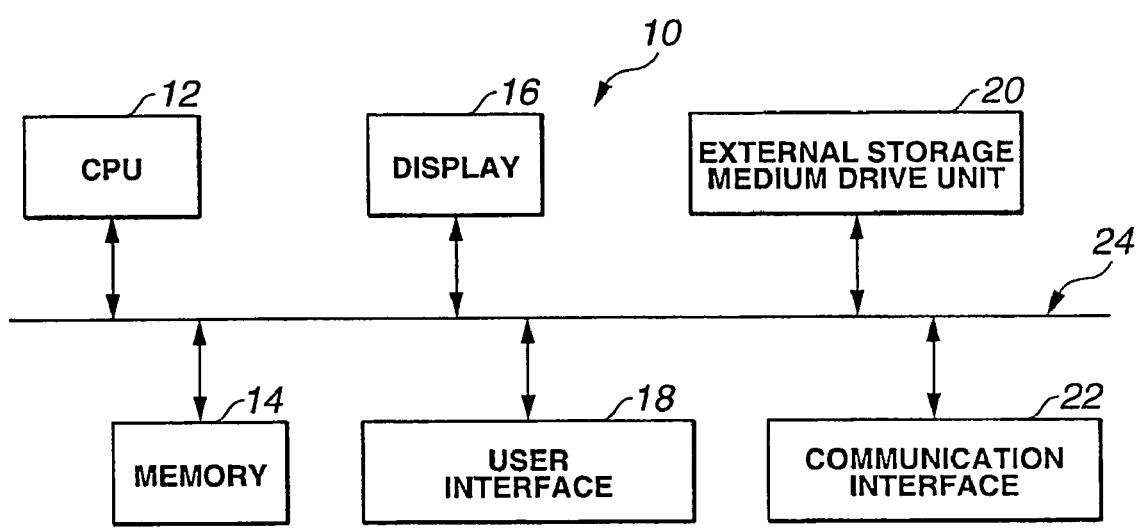
FIG. 1 shows a drawing of the hardware structure for the computer executing quantitation of protein contents based on the above EMPAI according to the present invention.

FIG. 1 shows a drawing of the hardware structure for the computer carrying out quantitation of protein contents based on the above EMPAI by the LC-MS according to the present invention. An analytical apparatus 10 for executing quantitation of protein contents based on the EMPAI according to the present invention comprises a central processing unit 12 (hereinafter abbreviated as "CPU"), a memory 14, a display device 16, a user interface 18, and a communication interface 22, all mutually connected via a bus 24 with the CPU 12. The apparatus 10 further comprises an external storage (not shown in FIG. 1), such as a CD-ROM or a magnetic medium, connected to an external storage medium drive unite 20. The apparatus 10 can be connected to the external data base, such as NCBInr (http://www.ncbi.nlm.nih.gov/) and so on, through the communication interface 22. The apparatus 10 can also be connected to the mass spectrometric device via the communication interface 22, which carries out analysis of the proteins.

Figure 2:
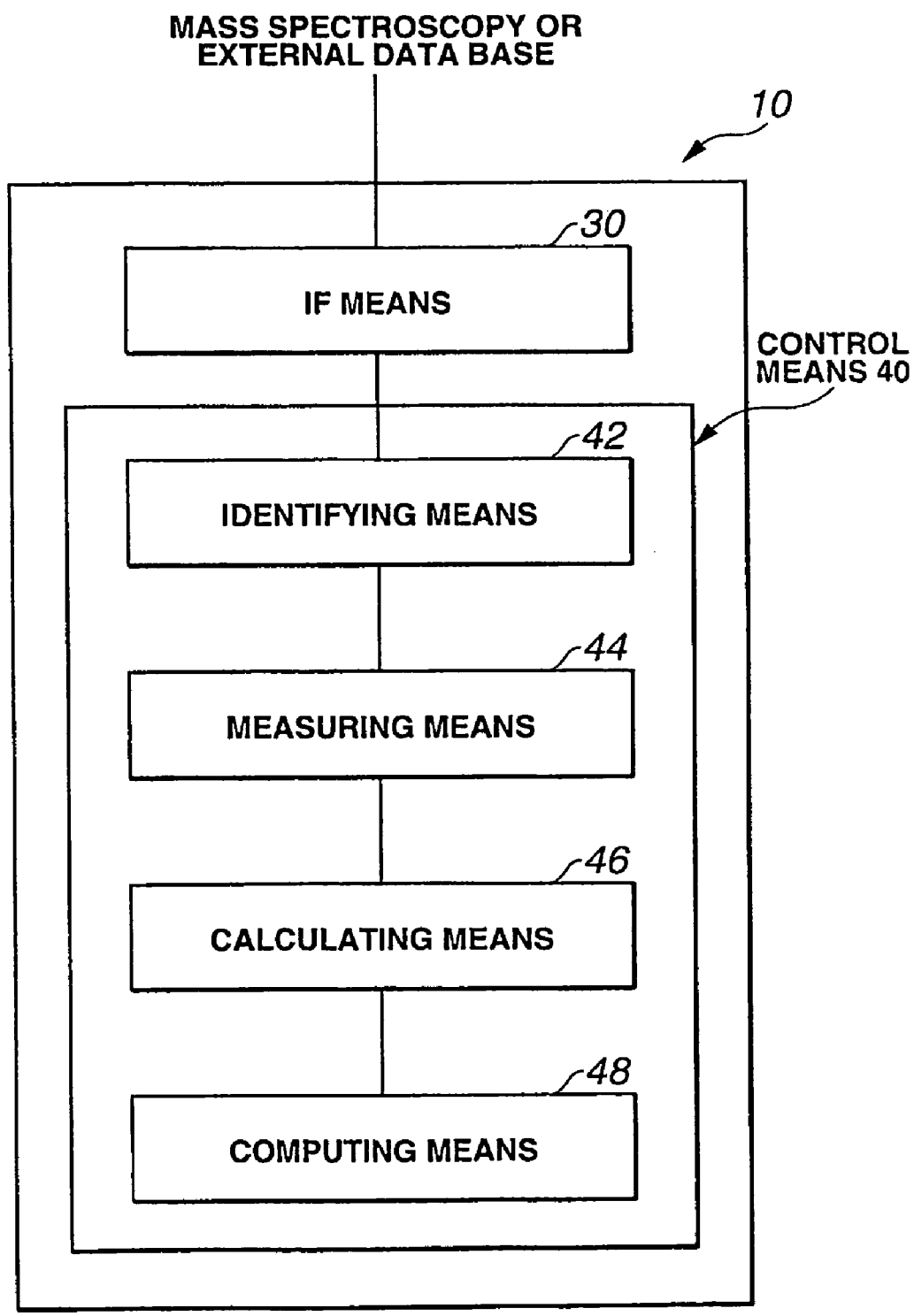
FIG. 2 shows a block diagram which is used to illustrate the construction of an analytical apparatus for executing quantitation of protein contents based on the EMPAI according to the present invention.

FIG. 2 shows a block diagram which is used to illustrate the construction of the analytical apparatus 10 for executing quantitation of protein contents based on the EMPAI according to the present invention. As is shown in FIG. 2, the apparatus 10 comprises IF (interface) means 30 and control means 40. The apparatus 10 is constructed so that these means 30, 40 receive input, for example, a mass spectrometric data, from the user utilizing this apparatus and/or a mass spectrometry, and output information to this user and/or the mass spectrometry. An ordinary personal computer can be used as the apparatus 10. Examples of the mass spectrometric data include a mass spectrum, a mass chromatogram and MSMS data and so on.

The IF means 30 is constructed so that information can be input and output with respect to input device such as a keyboard, the mass spectrometry or the like and output device such as a display, printer or the like. Via the IF means 30, the mass spectrometric data to be analyzed is transmitted to the control means 40.

The control means 40 comprises identifying means 42, measuring means 44, calculating means 46 and computing means 48. In the present invention, the identifying means 42 can receive information as to mass spectrometric data of proteins via the IF means 30 and identifies a protein to be quantified by mass spectrometry. Next, based on the mass spectrometric data, the measuring means 44 measures the number of observed peptides per the protein ($N_{obsd}$) which has been identified by the identifying means 42. On the other hand, based on identification of the protein to be quantified, calculating means 46 calculates the number of observable peptides per protein ($N_{obsbl}$). Here, the term "the number of observed peptides per protein" used herein means that the number of peptides per protein to be quantified which was actually observed by the mass spectrometry. The term "the number of observable peptides per protein" used herein means that a theoretical number of peptides per the protein. It should be noted that these numbers are defined in the document [17].

In the method according to the present invention, based on $N_{obsd}$ and $N_{obsbl}$ values, the computing means 48, which receives information as to $N_{obsd}$ and $N_{obsbl}$, computes the following equation to obtain EMPAI:

$$EMPAI = 10^{N_{obsd}/N_{obsbl}} - 1$$

As a result, according to the present invention, it is established that the exponentially modified protein abundance index ("EMPAI"), which is proportional to protein contents in the protein mixture, to determine the protein contents.

In addition, the computing means 48 calculates protein contents (mol %) and protein contents (weight %) in accordance with the two equations as follows:

$$\text{protein contents (mol \%)} = \frac{EMPAI}{\sum (EMPAI)} \times 100,$$

$$\text{protein contents (weight \%)} = \frac{EMPAI \times MW}{\sum (EMPAI \times MW)} \times 100,$$

wherein $\Sigma(EMPAI)$ is the summation of EMPAI values for all identified proteins and MW represents molecular weight of each protein identified.

According to need, the computed and/or calculated data can be stored in memory means, which is not shown in FIG. 2.

Figure 3:
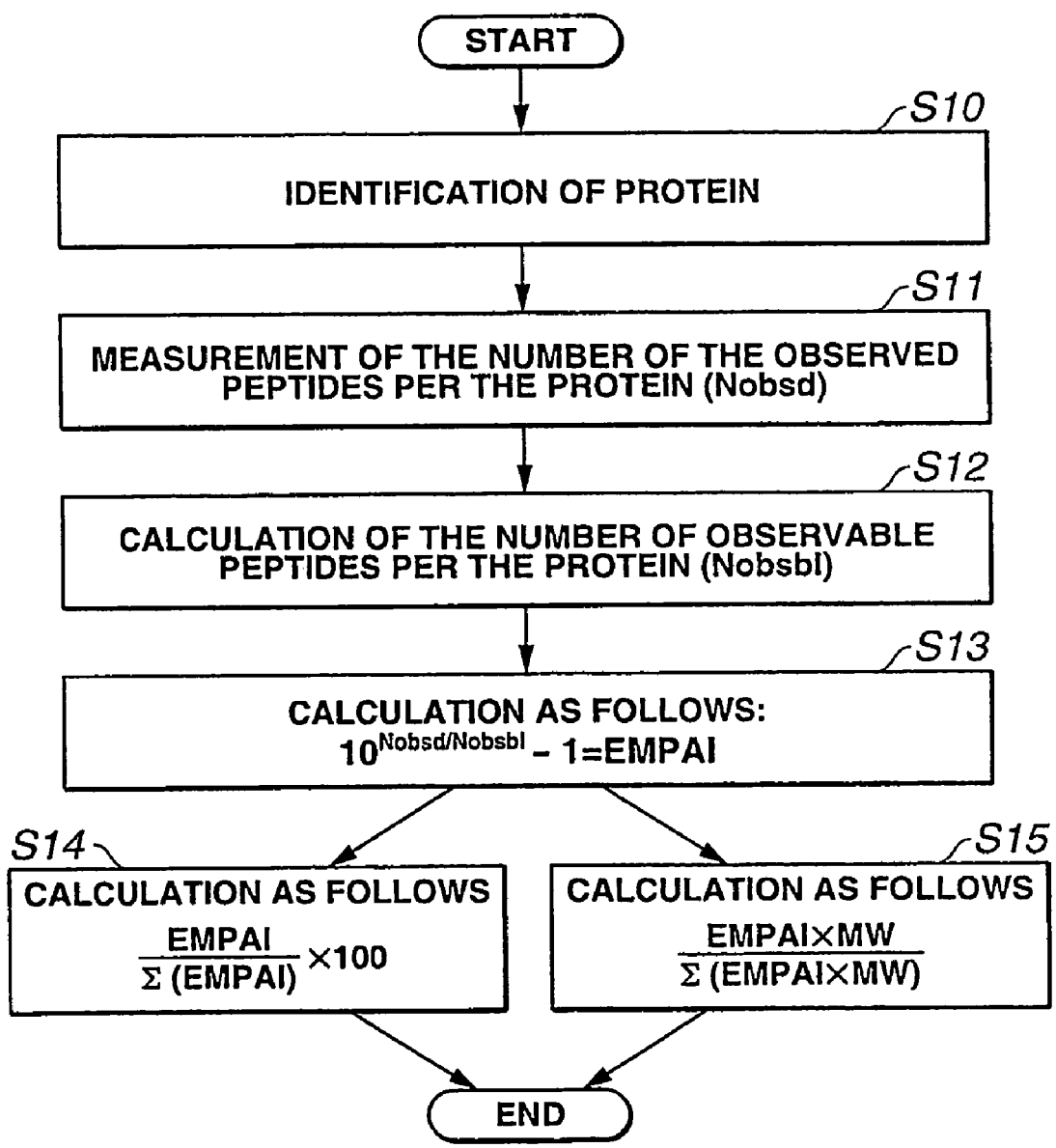
FIG. 3 shows a flowchart for executing quantitation of protein contents based on the EMPAI according to the present invention.

FIG. 3 shows a flowchart for executing quantitation of protein contents based on the EMPAI according to the present invention. In the step S10, a protein of interest is identified by the identifying means 42 after performing the mass spectrometry of samples of the biological materials by a MS method. This MS method includes peptide mass fingerprinting method and MS/MS method. It is understood by those skilled in the art that as disclosed in the following documents (Proc. Natl. Acad. Sci. USA. 1993, 90, 5011-5015, J. Curr. Biol. 1993, 3, 327-332, Biol. Mass. Spectrom. 1993, 22, 338-345, Nat Genet. 1998: 20, 46-50; J Cell Biol. 1998:141, 967-977; J Cell Biol, 2000:148, 635-651; Nature. 2002: 415.141-147; Nature, 2002: 415, 180-183; Curr Opin Cell Biol. 2003: 15, 199-205; Curr Opin Chem Biol. 2003: 7, 21-27, which are incorporated by reference in their entirety). In the next step S11, the number of the observed peptides per the protein identified above is measured by the measuring means 44 with use of the MS data. Then, the number of observable peptides per the protein is calculated by the calculating means 46 based on the structure of the protein identified above (as shown in step S12). It is possible to calculate the number of observable peptides per the protein prior to measurement of the observed peptides per the protein.

Figure 4:
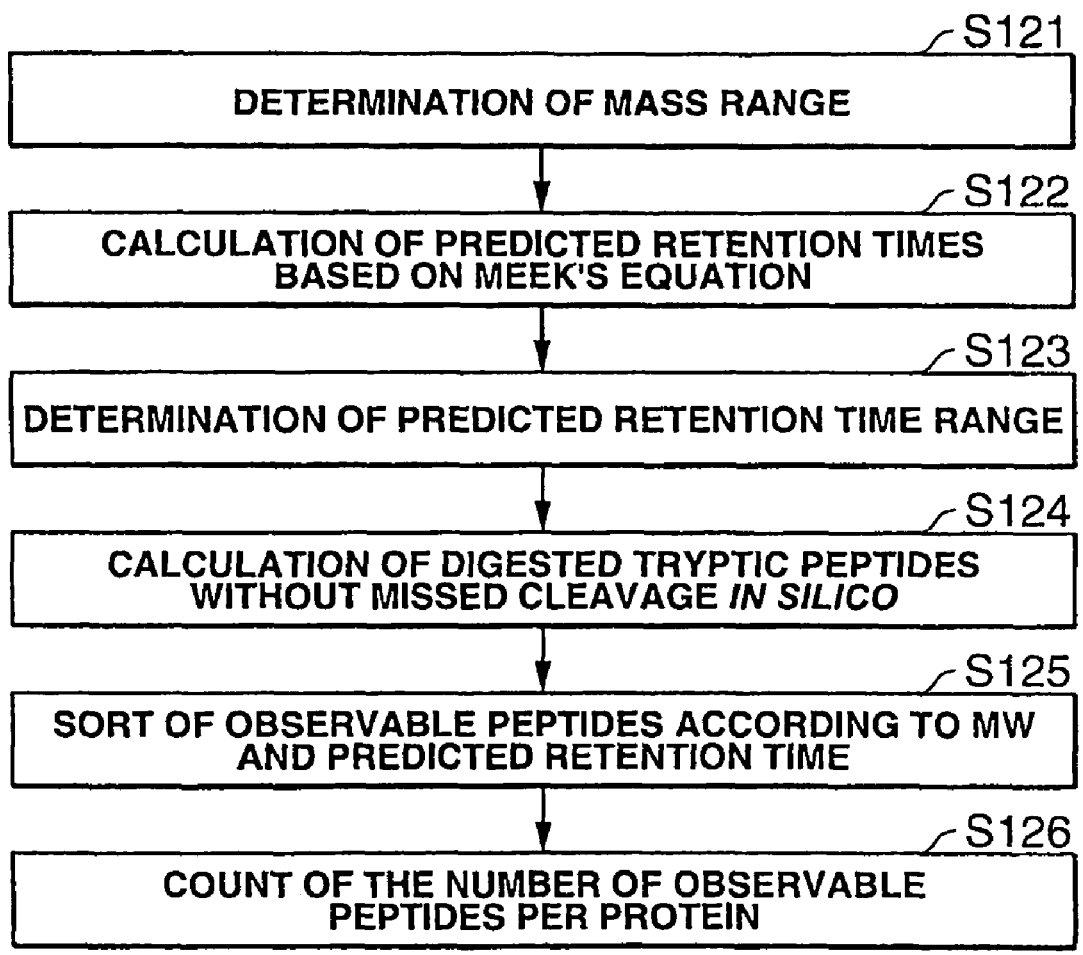
FIG. 4 shows one example of a flowchart for calculating the number of observable peptides per the protein.

FIG. 4 shows one example of a flowchart for calculating the number of observable peptides per the protein, which is used in the present invention. In the step S121, the mass range is determined by using the observed peptides and the scan range of mass spec. In the next step S122, the predicted retention times in each observed peptides are calculated based on Meek's equation (as described in [23]). Note that amino acid sequence of each observed peptides can be determined, for example, by the MS/MS method and according to the Meek's equation, there is the relationship between the known amino acid sequence and the retention time in liquid chromatography. Then, in the step S123, the predicted retention time range is determined by using a retention time of observed peptides, based on the above Meek's equation. Then, the digested tryptic peptides without missed cleavage are calculated in silico (in step S124). More specifically, since trypsin is famous protease by which the peptide bond can selectively be cleaved at the carboxylic side of lysine residue and arginine residue in the protein, there is determined amino acid sequences of the digested tryptic peptides without missed cleavage. Thus, in this step S124, molecular weight (MW) and predicted retention time of the digested tryptic peptides are calculated in silico. In the next step S125, the observable peptides are sorted according to the MW and the predicted retention time. Finally, in the step S126, the number of observable peptides per protein is counted, on the basis that MW and the predicted retention time of the observable peptides fall both within the mass range (in S121) and retention time range (in S123).

It should be noted that in the present invention, there is no limitation on calculation of the number of observable peptides which is carried out according to the flowchart of FIG. 4.

By use of the number of the observed peptides per the protein ($N_{obsd}$) and the number of observable peptides per the protein ($N_{obsbl}$), an EMPAI is calculated by the computing means 48 as follows (in step S13):

$$EMPAI = 10^{N_{obsd}/N_{obsbl}} - 1$$

Using the value of EMPAI, protein contents in molar and weight percentage are expressed as follows:

$$\text{Protein contents (mol \%)} = \frac{EMPAI}{\sum(EMPAI)} \times 100$$

$$\text{Protein contents (weight \%)} = \frac{EMPAI \times MW}{\sum(EMPAI \times MW)} \times 100$$

wherein MW is the molecular weight of each protein identified, and $\Sigma(EMPAI)$ is the summation of EMPAI values for all identified proteins (as shown in Steps 14 and 15).

A program which executes the flow of the analysis of protein contents illustrated in FIG. 3, which is discussed above, is stored in the memory 14 or the external storage via the external storage medium drive unit 20 or is directly transferred to the CPU 12 in case where the program is stored in the external storage medium, such as the CD-ROM.

It should be noted that prior to the quantitation according to the present invention, the protein is identified by the reference to the external database, such as NCBlnr database, through the communication interface 22. According to need, the display device 16 displays results of the quantitation according to the present invention via the user interface 18.

In this way, the present invention provides the method for executing quantitation of the protein contents based on the EMPAI and computer program for performing the above method.

The following will be given of typical examples according to aspects of the present invention, however, the scope of the present invention is not intended to be limited thereto.

MATERIALS AND METHODS

Preparation of Cell Lysate.

RPMI-1640 media (Gibco BRL, Grand Island, N.Y.) containing $^{13}C_6$-Leu (Cambridge Isotope Laboratories, Andover, Mass.) were prepared according to SILAC protocol by Ong et al. [4]. Mouse neuroblastoma neuro2a cells were cultured for $^{13}C_6$-Leu labeling in this medium. Whole proteins were lysed using ultrasonication with protease inhibitor cocktail (Roche Diagnostics, Basel, Switzerland). HCT116-C9 cells were grown in a normal RPMI 1640 culture medium as described [10]. Whole proteins were extracted with 5 mL of M-PER (Pierce, Rockford, Ill., USA) containing protease inhibitor cocktail and 5 mM dithiothreitol.

Preparation of Peptide Mixtures for LCMSMS.

Proteins from cells were dried down and re-suspended by 50 mM Tris-HCl buffer (pH 9.0) containing 8M urea. These mixtures were subsequently reduced, alkylated, and digested by Lys-C (Wako, Osaka, Japan) and trypsin (Promega, Madison, Wis., USA) as described [6]. Digested solutions were acidified by TFA, and were desalted and concentrated by C18-StageTips[21], which were prepared by a fully-automated instrument (Nikkyo Technos, Tokyo, Japan) with Empore C18 disks (3M, Minn., USA). Candidates for peptide synthesis containing at least one leucine and one tyrosine were selected considering the sequences of tryptic peptides from proteins expressed in neuro2a cells. Peptides containing methionine and tryptophan were removed to avoid the oxidation problems during sample preparation. In addition, peptides with double basic residues were removed considering the frequent missed cleavage by trypsin. The selected 54 peptides were synthesized using a Shimadzu PSSM8 (Kyoto, Japan) with F-moc chemistry and were purified by preparative HPLC. Amino acid analysis, peptide mass measurement and HPLC-UV were carried out for purity and structure elucidation. Different amounts of these peptides were spiked to the peptide mixtures from neuro2a cells and purified by StageTip as described above.

NanoLC-MS/MS Analysis

All samples were analyzed by nanoLC-MS/MS using a QSTAR Pulsar i (ABI/MDS-Sciex, Toronto, Canada) or Finnigan LCQ advantage (Thermoelectron, San Jose, Calif., USA) equipped with a Shimadzu LC10A gradient pump, and an HTC-PAL autosampler (CTC Analytics AG, Zwingen, Switzerland) mounting Valco C2 valves with 150 μm ports. ReproSil C18 materials (3 μm, Dr. Maisch, Ammerbuch, Germany) were packed into a self-pulled needle (100 μm ID, 6 μm opening, 150 mm length) with a nitrogen-pressurized column loader cell (Nikkyo) to prepare an analytical column needle with "stone-arch" frit [22]. A Teflon-coated column holder (Nikkyo) was mounted on. Proxeon x-y-z nanospray interface (Odense, Denmark) and a Valco metal connector with magnet was used to hold the column needle and to adjust the appropriate spray position. The injection volume was 3 μL and the flowrate was 250 nL/min after a tee splitter. The mobile phases consisted of (A) 0.5% acetic acid and (B) 0.5% acetic acid and 80% acetonitrile. The three-step linear gradient of 5% B to 10% in 5 min, 10% to 30% in 60 min, 30% to 100% in 5 min and 100% in 10 min was employed through this study. Spray voltage of 2400 V was applied via the metal connector as described [22]. For QSTAR with faster scan mode, MS scans were performed for 1 second to select three intense peaks and subsequent three MSMS scans were performed for 0.55 seconds each. An Information Dependent Acquisition (IDA) function was active for three minutes to exclude the previously scanned parent ions. For slower scan mode, four MSMS scans (1.5 s each) per one MS scan (1 s) were performed. For LCQ, two MSMS scans per one MS scan were performed with AGC mode. The average scan cycle was 1.19 s for one MS and 1.17 s for one MSMS in average, respectively. The scan range was m/z 300-1400 for both QSTAR and LCQ.

DATA Analysis

Custom-made software called Spice (Mitsui Knowledge Industry, Tokyo, Japan) was used to extract all peaks from raw data files of both LCQ and QSTAR, and the resultant peak files were submitted to Mascot ver1.9 database searching engine (Matrix Sciences, London, UK; D. M. Perkins, D. J. Pappin, D. M. Creasy, J. S. Cottrell, Electrophoresis 20 (1999) 3551, which is incorporated by reference in its entirety.) for protein identification against Swiss-Prot protein database. The allowed number of missed cleavage set to be 1, and peptide scores to indicate identity was used for peptide identification without manual inspection of MSMS spectra. MSQuant ver1.4a was downloaded from http://msquant.sourceforge.net/, and was customized for $^{13}C_6$ Leu SILAC in order to determine the ion counts in chromatograms for absolute concentration of proteins using the known amounts of the synthetic peptides.

Protein Abundance Determination

To calculate the number of observable peptides per protein, proteins were digested in silico and the obtained peptide mass was compared with the measurement scan range of mass spectrometers. In addition, the retention times under our nanoLC condition were calculated according to the procedure by Meek [23] and Sakamoto et al.[24] with our own coefficients based on approximately 3000 peptides, and peptides with too hydrophilic or hydrophobic properties were eliminated. An in-house PHP program based on the following equations (1) to (4) was written to calculate the peptide number and was used to export all data to Microsoft Excel. Regarding the number of observed peptides per protein, three counting ways were employed, such as (1) to count unique parent ions, (2) to count unique sequences, and (3) to count unique sequences without partial modification and the overlap caused by missed cleavage. These numbers were exported from Mascot html files to Excel spreadsheets using an "Export All Peptides" function of MSQuant.

PAI is Defined As $$PAI = \frac{N_{obsd}}{N_{obsbl}} \quad (1)$$

wherein $N_{obsd}$ and $N_{obsbl}$ are the number of observed peptides per protein and the number of observable peptides per protein, respectively[17]. Then, EMPAI is defined as $$EMPAI = 10^{PAI} - 1 \quad (2)$$

Thus, the protein contents in molar and weight percentages are described as $$\text{Protein contents (mol \%)} = \frac{EMPAI}{\sum(EMPAI)} \times 100 \quad (3)$$

$$\text{Protein contents (weight \%)} = \frac{EMPAI \times MW}{\sum(EMPAI \times MW)} \times 100 \quad (4)$$

wherein MW is the molecular weight of each protein identified, and Σ EMPAI is the summation of EMPAI values for all identified proteins.

DNA Microarray Analysis.

HCT116-C9 cells were plated at $5.0 \times 10^6$ cells/dish in 10-cm diameter dishes with 10 mL of the culture medium. After 24-h preincubation, the cells were treated for 12 h with 0.015% DMSO. Duplicate experiments were performed using Affymetrix HuGene FL arrays according to established protocols. Affymetrix GeneChip software was used to extract gene signal intensities, and two sets of data were grouped and averaged based on gene symbol.

The Number of Identified Peptides from Single Protein with Different Concentrations.

Figure 5A:
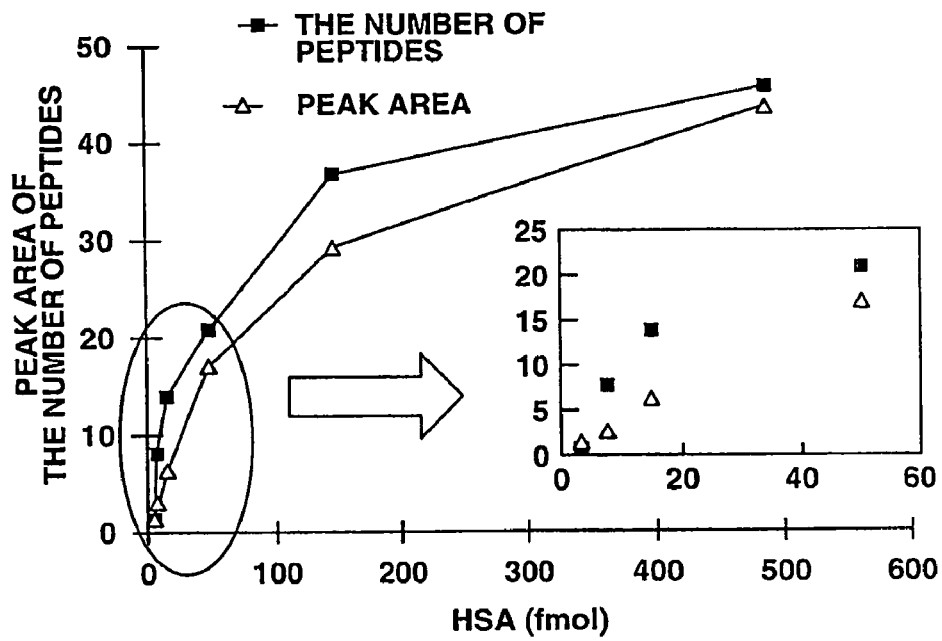
FIG. 5A shows peak area and the number of unique parent ions of peptides versus injection amounts of (HSA).
Figure 5B:
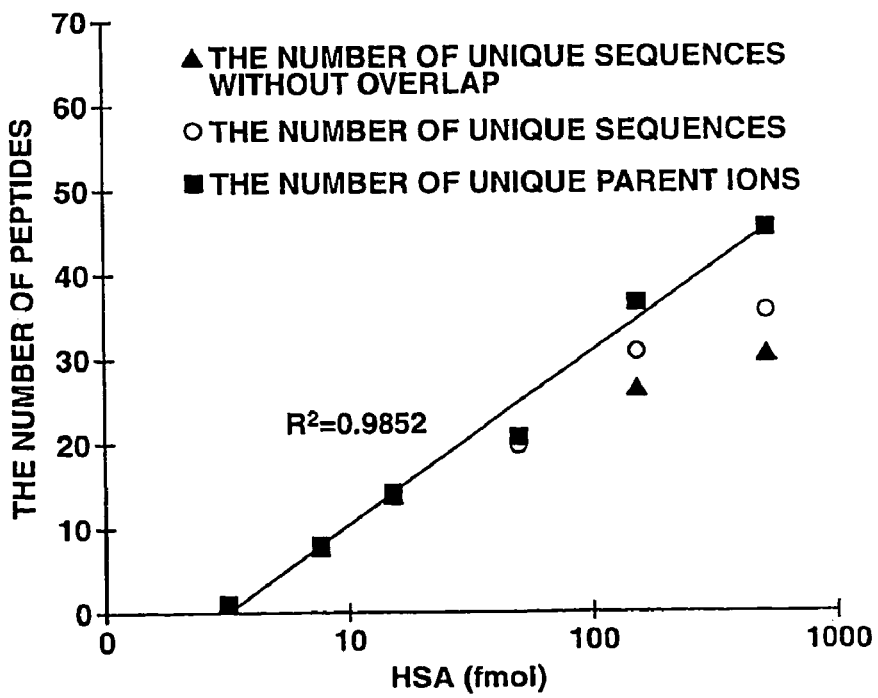
FIG. 5B shows three different numbers of peptides versus injection amounts of HSA.

Different amounts of human serum albumin (HSA) tryptic peptides were analyzed by nanoLC-ESI-MS/MS and the number of identified peptides was counted. As shown in FIG. 5A, both peak area and the number of identified peptides increased as the injection amounts increased although both curves were saturated at higher concentration of HSA. However even at the region where the peak area is linear, the number of peptides does not have linear relationship to the protein amount. Interestingly, the number of peptides shows linear relationship to logarithm of the injected amount from 3 fmol to 500 fmol (FIG. 5B). The same data was obtained from LCQ with slower scan. It means that each peak was well separated in time and the influence of "random sampling" caused by the slower scan did not happen under this condition. In this case, three ways were used to count peptides, i.e., (1) all parent ions including different charge states from the same peptide sequences, (2) all peptides excluding different charge states, partial modification such as methionine oxidation, (3) peptides with unique sequence excluding peptides overlapped by missed cleavage. Among them, the number of peptides based on unique parent ions gives the best correlation to the logarithm of protein abundance. It is believed that the results were not under the particular conditions, but more general phenomena. Recently, two independent groups presented the similar curves between the number of peptides and the concentration of proteins. Although both of them did not analyze the logarithm of proteins, but in our hand, their data also looked the linear relationship between logarithm of protein concentration and the number of peptides. The reason why the logarithm of protein concentration correlates to the number of digested peptides is not clear, but it might be explained by the fact that chemical potential is proportional to the logarithm of concentration and the required energy for ionization of peptides is linearly increased as the chemical potential increased.

PAI of 47 Proteins in Highly Complex Mixture Solutions

Next, the present inventor investigated 54 proteins with known amounts in a whole cell lysate. Tryptic peptides from mouse neuroblastoma neuro2a cell labeled with $^{13}C_6$-Leu were measured by a single LC-MS/MS run with QSTAR, and 336 proteins were identified based on 1462 peptides. The present inventor spiked 54 synthetic peptides containing $^{12}C_6$-Leu to this sample solution and quantified the corresponding tryptic peptides containing $^{13}C_6$-Leu. Seven peptides were not quantified because they gave overlapped peaks in the extracted ion chromatograms (XIC). As a result, 47 proteins with 13K-229 KDa in molecular weight were quantified in the range from 30 fmol to 1.8 pmol/μL in the sample solution as listed in Tables 1A and 1B.

TABLE 1A

| Acc NO | NAME | MASCOT HIT# | MW | INJECTION AMOUNT (fmol) | THE NUMBER OF PEPTIDES | MASCOT SCORE | PAI | EMPAI |
|---|---|---|---|---|---|---|---|---|
| P19378 | Heat shock cognate 71 kDa protein | 1 | 70989 | 2055 | 29 | 1235 | 0.88 | 6.56 |
| P07901 | Heat shock protein HSP 90-alpha | 2 | 85003 | 2351 | 31 | 1047 | 0.86 | 6.26 |
| P20152 | Vimentin | 5 | 53581 | 840 | 27 | 1080 | 0.82 | 5.58 |
| P58252 | Elongation factor 2 (EF-2) | 6 | 96091 | 295 | 24 | 830 | 0.53 | 2.41 |
| Q03265 | ATP synthase alpha chein, mitochondrial precursor | 8 | 59830 | 371 | 18 | 635 | 0.56 | 2.65 |
| P17182 | Alpha enolase | 9 | 47322 | 1491 | 21 | 828 | 0.88 | 6.50 |
| P15331 | Peripherin | 10 | 54349 | 209 | 13 | 556 | 0.39 | 1.48 |
| P48975 | Actin, cytoplasmic 1 (Beta-actin) | 12 | 42053 | 3015 | 22 | 894 | 1.22 | 15.66 |
| P05213 | Tubulin alpha-2 chain (Alpha-tublin 2) | 14 | 50818 | 4455 | 24 | 862 | 1.14 | 12.89 |
| P52480 | Pyruvate kinase, M2 isozyme | 16 | 58289 | 539 | 17 | 643 | 0.49 | 2.06 |
| P20001 | Elongation factor 1-alpha 1 | 24 | 50424 | 2176 | 17 | 647 | 1.00 | 9.00 |
| P08113 | Endoplasmin presursor | 25 | 92703 | 225 | 10 | 379 | 0.23 | 0.71 |
| O35501 | Stress-70 protein, mitochodrial precursor | 27 | 73970 | 488 | 15 | 495 | 0.38 | 1.42 |
| P14869 | 60S acidic ribosomal protein P0 | 34 | 34336 | 255 | 9 | 379 | 0.50 | 2.16 |
| P03975 | igE-binding protein | 35 | 63221 | 306 | 10 | 368 | 0.33 | 1.15 |
| Q9CZD3 | Glycyl-tRNA synthetase | 37 | 82624 | 193 | 9 | 341 | 0.21 | 0.62 |
| P35215 | 14-3-3 protein zeta/delta | 40 | 27925 | 952 | 12 | 401 | 0.75 | 4.62 |
| P42932 | T-complex protein 1, theta, subunit | 42 | 60088 | 240 | 9 | 281 | 0.26 | 0.81 |
| P51881 | ADP, ATP carrier protein, fibrobiast isoform | 46 | 33138 | 660 | 8 | 294 | 0.42 | 1.64 |
| Q9JIK5 | Nucleolar RNA helicase II | 48 | 94151 | 75 | 8 | 268 | 0.16 | 0.45 |
| P14148 | 60S ribosomal protein L7 | 52 | 31457 | 300 | 9 | 227 | 0.53 | 2.38 |
| Q9WVA4 | Transgelin 2 | 65 | 23810 | 324 | 8 | 258 | 0.62 | 3.12 |
| P14211 | Calreticulin precursor | 72 | 48136 | 285 | 8 | 246 | 0.33 | 1.15 |
| P16858 | Glyceraldehyde 3-phosphate dehydrogenase | 87 | 35941 | 1000 | 8 | 270 | 0.53 | 2.41 |

TABLE 1B

| Acc NO | NAME | MASCOT HIT# | MW | INJECTION AMOUNT (fmol) | THE NUMBER OF PEPTIDES | MASCOT SCORE | PAI | EMPAI |
|---|---|---|---|---|---|---|---|---|
| P29314 | 40S ribosomal protein S9 | 88 | 22418 | 338 | 6 | 201 | 0.46 | 1.89 |
| Q60932 | Voltage-dependent anion-selective channel protein | 89 | 32502 | 180 | 6 | 261 | 0.38 | 1.37 |
| P17080 | GTP-bilding nuclear protein RAN | 97 | 24579 | 638 | 5 | 181 | 0.45 | 1.85 |
| P17008 | 40S ribosomal protein S16 | 98 | 16418 | 1140 | 6 | 174 | 0.60 | 2.98 |
| Q60930 | Voltage-dependent anion-selective channel protein | 99 | 32340 | 135 | 4 | 161 | 0.27 | 0.85 |
| P11983 | T-complex protein 1, alpha subunit B | 100 | 60867 | 90 | 6 | 143 | 0.18 | 0.52 |
| P05064 | Fructose-bisphosphate aldolase A | 103 | 39656 | 525 | 6 | 260 | 0.33 | 1.15 |
| P09058 | 40S ribosomal protein S8 | 109 | 24344 | 240 | 6 | 186 | 0.60 | 2.98 |
| Q01320 | DNA topoisomerase II, alpha isozyme | 143 | 173567 | 90 | 4 | 125 | 0.05 | 0.12 |
| Q8VEM8 | Phosphate carrier protein, mitochondrial precursor | 149 | 40063 | 120 | 4 | 122 | 0.19 | 0.55 |
| P19253 | 60S ribosomal protein L13a | 150 | 23432 | 120 | 4 | 123 | 0.33 | 1.15 |
| P08526 | 60S ribosomal protein L27 | 157 | 15657 | 214 | 3 | 113 | 0.50 | 2.16 |
| P47961 | 40S ribosomal protein S4 | 160 | 29666 | 405 | 4 | 109 | 0.21 | 0.62 |
| Q06647 | ATP synthase ollgomycin sensitivity conferral protein | 179 | 23440 | 195 | 3 | 98 | 0.23 | 0.70 |
| Q9CPR4 | 60S ribosomal protein L17 | 182 | 21506 | 225 | 3 | 96 | 0.30 | 1.00 |
| P39026 | 60S ribosomal protein L11 | 186 | 20337 | 270 | 3 | 92 | 0.33 | 1.15 |
| Q9D1R9 | 60S ribosomal protein L34 | 204 | 13381 | 240 | 3 | 83 | 0.50 | 2.16 |
| O08807 | Peroxiredoxin 4 | 206 | 31261 | 180 | 4 | 83 | 0.27 | 0.85 |
| Q62188 | Dihydropyrimidinase related protein-3 | 207 | 62296 | 75 | 3 | 82 | 0.10 | 0.27 |
| P50310 | Phosphoglycerate kinase | 213 | 44776 | 75 | 3 | 80 | 0.13 | 0.33 |
| Q9DBJ1 | Phosphoglycerate mutase 1 | 223 | 28797 | 285 | 3 | 70 | 0.25 | 0.78 |
| P11442 | Clathrin heavy chain | 226 | 193187 | 137 | 3 | 69 | 0.04 | 0.09 |
| QPJLT0 | Myosin heavy chain, nonmuscle type B | 305 | 229793 | 87 | 1 | 45 | 0.01 | 0.02 |

In this case, two additional factors should be considered. One is the influence of protein size on the number of peptides. Generally larger proteins generate more detectable peptides.

Figure 6A:
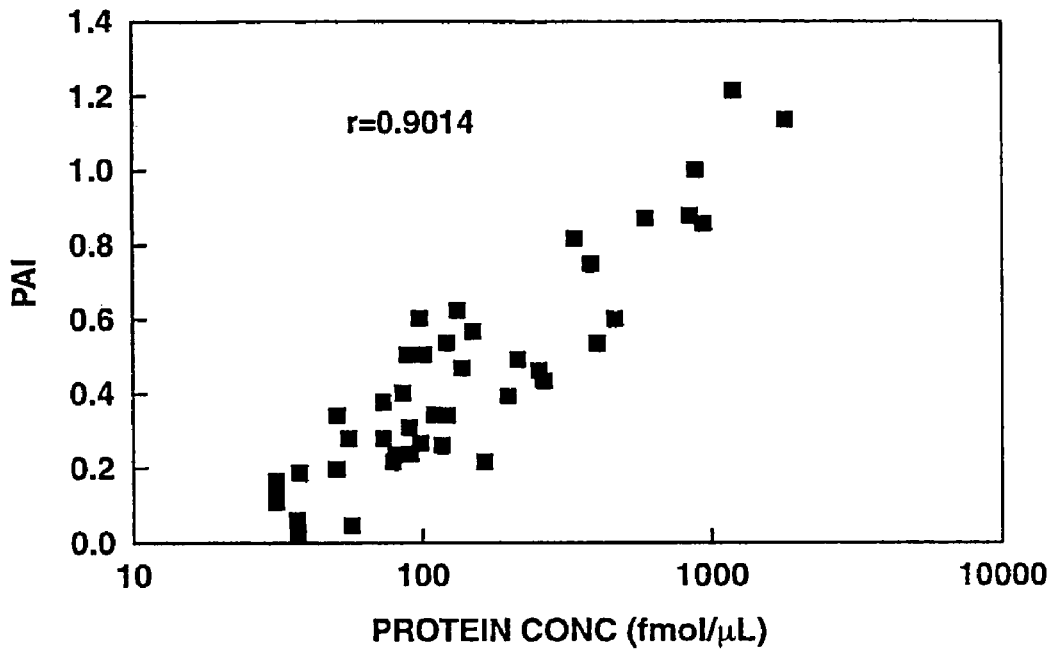
FIG. 6A shows protein concentrations versus PAI.
Figure 6B:
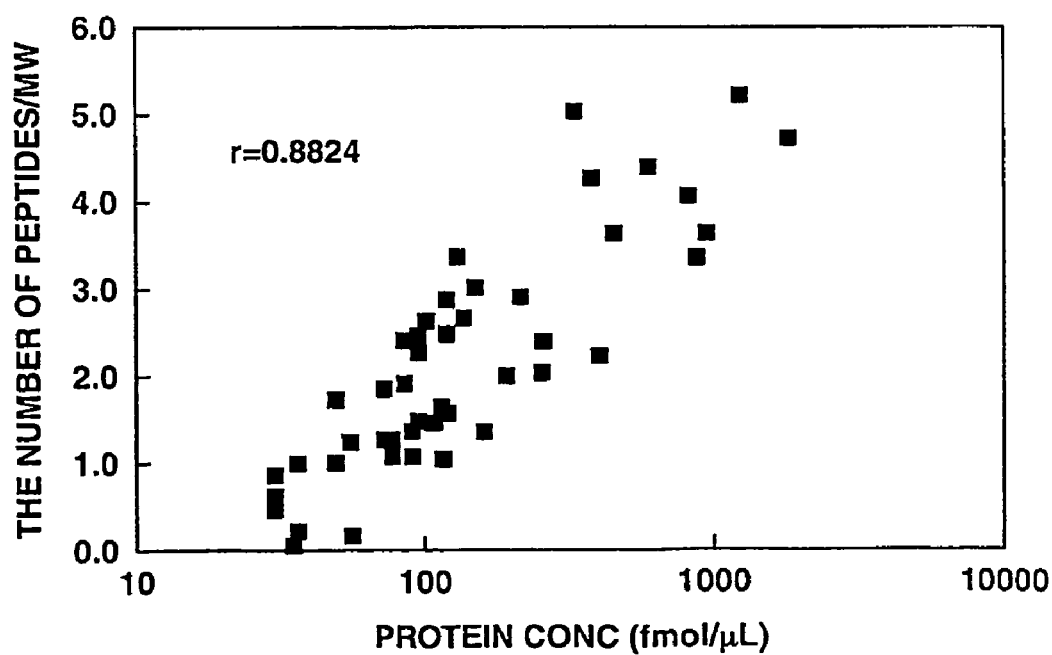
FIG. 6B shows protein concentration versus the number of peptides divided by molecular weight of proteins.
Figure 6C:
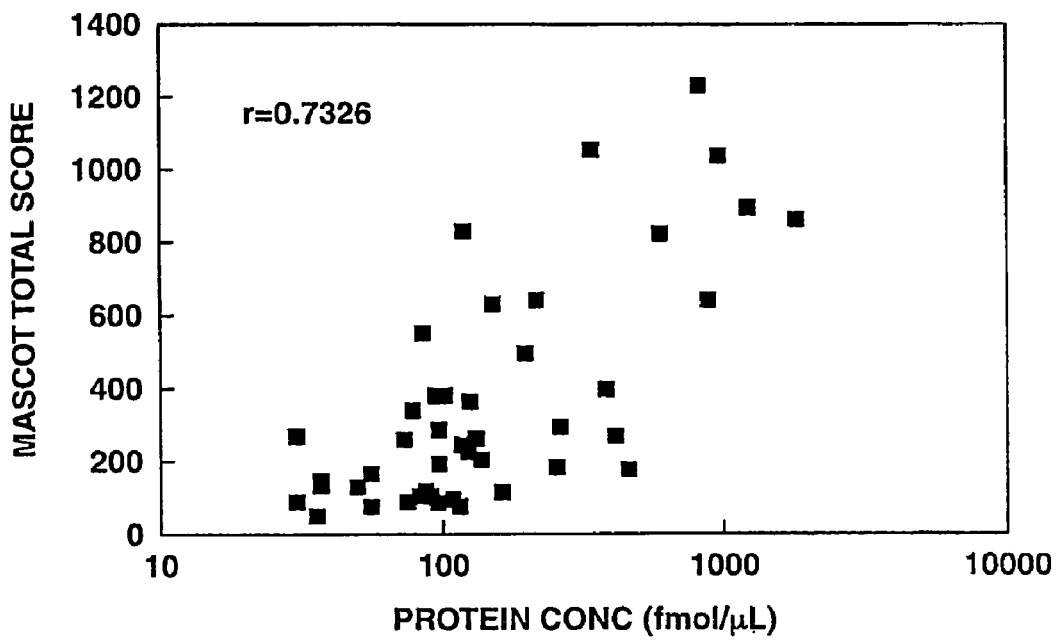
FIG. 6C shows protein concentration versus Mascot score.
Figure 6D:
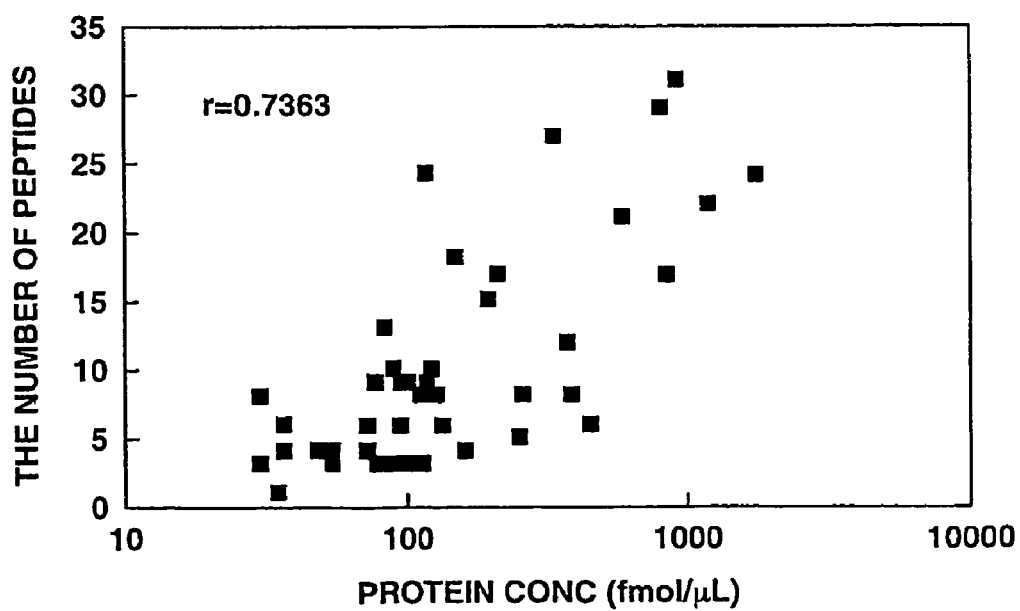
FIG. 6D shows protein concentration versus the number of observed peptides (unique parent ions)

Therefore, observable peptides were used for normalization as previously except the additional criteria on retention times. Another factor was the background. In this case, a huge number of peptides existed in the sample. Therefore, the number of observed peptides would be to some extent influenced by the ionization suppression effect as well as the random selection for MSMS events. FIG. 6A shows that there is also a linear relationship between log [protein] and the number of observed peptides normalized by the number of observable peptides per protein even when the different proteins were plotted into one graph. Other parameters such as Mascot score and the number of peptides do not correlate well to protein abundance, and the number of peptides divided by molecular weight of protein gives moderate correlation to logarithm of protein contents, as shown in FIGS. 6B-D.

Figure 7A:
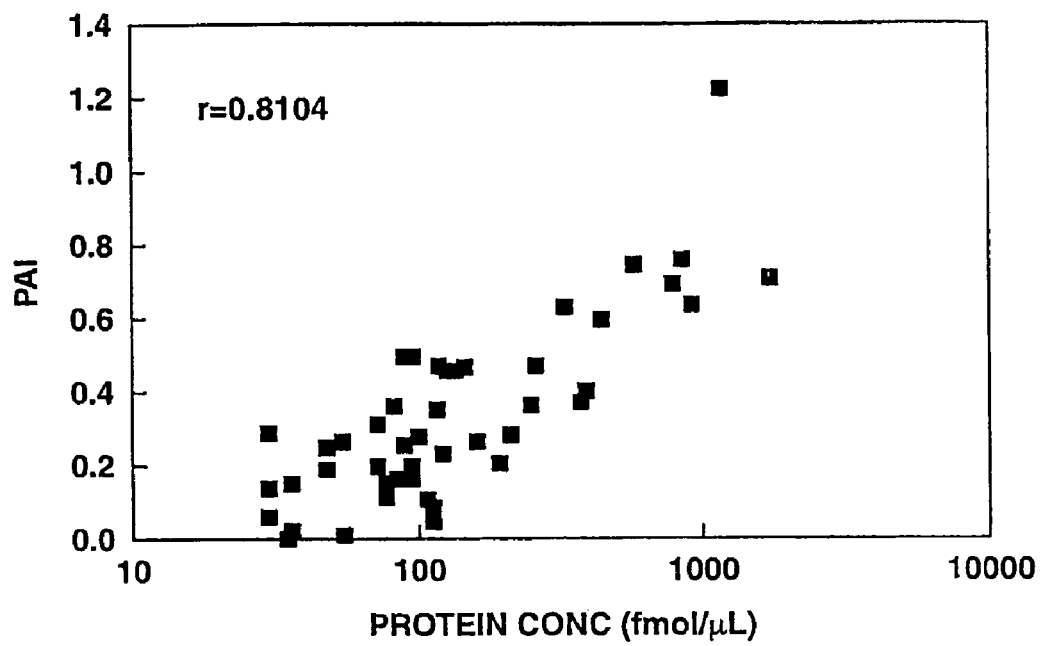
FIG. 7A shows time-of-flight type mass spectrometry (QSTAR) with slower scans.
Figure 7B:
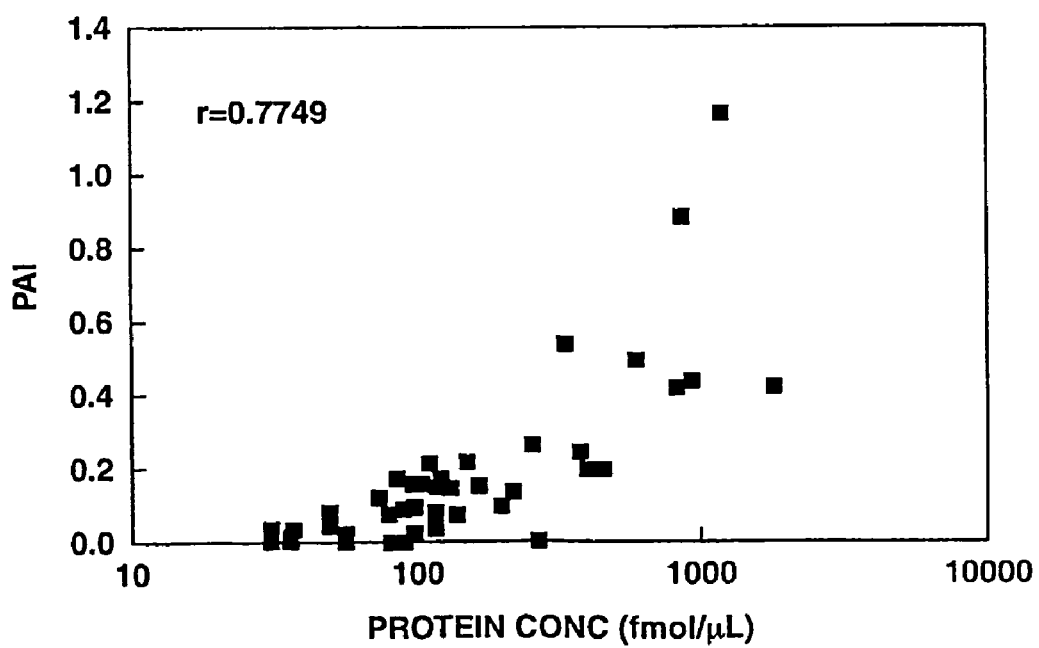
FIG. 7B shows ion trap type mass spectrometry (LCQ) with slower scans.

In this case, the present inventor used highest MSMS scan speed of QSTAR to minimize the background influence. When lower scan speed was used, the correlation was decreased (r=0.90 to 0.81). For example, refer to FIG. 7A. This effect was more pronounced when iontrap instrument was used (r=0.77). This would be because the limited amount of trap capacity causes more biased peak selection for more abundant proteins, and actually the larger deviation was observed for higher abundant proteins in FIG. 7B. Recent development of linear iontrap with higher capacity with faster scan would provide similar results to QSTAR with faster scan mode.

In addition, the influence of the sample complexity would be minimized by using multidimensional separation prior to MSMS analysis such as LC/LC-MS/MS [25] and GeLCMS (gel-enhanced LC-MS, 1D-gel followed by slicing, digesting and LCMS analysis) approaches [15].

Example of EMPAI Calculation

The whole protocol to calculate EMPAI values is as follows:
(1) Perform LC-MS/MS analysis;
(2) Identify proteins using search engines such as Mascot;
(3) Extract the number of unique parent ions per protein;
(4) Count the number of observable peptides per protein; and
(5) Calculate EMPAI value using (3) and (4).

The following is an example of EMPAI calculation by use of one typical example in Table 2.

TABLE 2

| Sample | human serum albumin, 150 fmol |
|---|---|
| Method | LC-MSMS |
| Search engine | Mascot |
| Protein database | SwissProt |

(3) Extraction of Observed Unique Parent Ions

The extraction of observed unique parent ions was performed following the above protocol (1) and (2). The results of the above extraction are tabulated in Table 3. In the column of "Accept or not" in Table 2, based on the results of Mascot score, the term "Yes" refers to extraction being carried out and the term "No" means that the observed parent ions was not extracted due to small Mascot score.

TABLE 3

| ALBU_HUMAN P02768 | Mass: | 71317 | Total score: | 1337 | Peptides matched: Serum albumin precursor | 37 | |
|---|---|---|---|---|---|---|---|
| Pept No | Observed | Mr(calc) | Missed cleavage | Score | Rank | Peptide | Accept or not | Comments |
| 1 | 395.2529 | 788.4643 | 0 | 35 | 1 | LVTDLTK | Yes | |
| 2 | 440.7369 | 879.4337 | 0 | 27 | 1 | AEFAEVSK | Yes | |
| 3 | 464.2663 | 926.4861 | 0 | 35 | 1 | YLYEIAR | Yes | |
| 4 | 467.2726 | 932.5113 | 0 | 40 | 1 | LCTVATLR | Yes | |
| 5 | 470.7521 | 939.441 | 0 | 60 | 1 | DDNPNLPR | Yes | |
| 6 | 476.2422 | 950.4345 | 0 | 10 | 1 | DLGEENFK | No | Score is less than the threshold. |
| 7 | 480.8003 | 959.5552 | 0 | 51 | 1 | FQNALLVR | Yes | |
| 8 | 492.7642 | 983.4811 | 0 | 3 | 1 | TYETTLEK | No | Score is less than the threshold. |
| 9 | 500.8268 | 999.5964 | 0 | 53 | 1 | QTALVELVK | Yes | |
| 10 | 507.3224 | 1012.5916 | 0 | 20 | 2 | LVAASQAALGL | No | Rank is not 1 |
| 11 | 509.2948 | 1016.5291 | 0 | 27 | 1 | SLHTLFGDK | Yes | |
| 12 | 535.7427 | 1069.4386 | 0 | 16 | 1 | ETCFAEEGK | Yes | |
| 13 | 537.7922 | 1073.5352 | 1 | 43 | 1 | LDELRDEGK | Yes | |
| 14 | 376.9148 | 1127.6913 | 1 | 17 | 1 | KQTALVELVK | Yes | Overlapped sequence with pept 9, but different parent ion |
| 15 | 564.8761 | 1127.6913 | 1 | 38 | 1 | KQTALVELVK | Yes | Same sequence as Pept14, but different charge |
| 16 | 569.7725 | 1137.4906 | 0 | 65 | 1 | CCTESLVNR | Yes | |
| 17 | 575.3179 | 1148.6077 | 0 | 60 | 1 | LVNEVTEFAK | Yes | |
| 18 | 599.7489 | 1197.5335 | 1 | 36 | 1 | ETCFAEEGKK | Yes | |
| 19 | 671.7959 | 1341.6274 | 0 | 86 | 1 | AVMDDFAAFVEK | Yes | |
| 20 | 679.7764 | 1357.6223 | 0 | 33 | 1 | AVMDDFAAFVEK + Oxidation(M) | Yes | Same sequence and charge as Pept20, but different parent ion because of modification |
| 21 | 686.267 | 1370.5594 | 0 | 56 | 1 | AAFTECCQAADK | Yes | |
| 22 | 717.7518 | 1433.5261 | 0 | 61 | 1 | ETYGEMADCCAK | Yes | |
| 23 | 722.3062 | 1442.6347 | 0 | 60 | 1 | YICENQDSISSK | Yes | |
| 24 | 749.7717 | 1497.5711 | 0 | 72 | 1 | TCVADESAENCDK | Yes | |
| 25 | 756.4021 | 1510.8354 | 0 | 19 | 1 | VPQVSTPTLVEVSR | Yes | |
| 26 | 820.4454 | 1638.9304 | 1 | 40 | 1 | KVPQVSTPTLVEVSR | Yes | |
| 27 | 547.3489 | 1638.9304 | 1 | 63 | 1 | KVPQVSTPTLVEVSR | Yes | Same sequence as Pept26, but different charge |
| 28 | 829.3597 | 1656.7453 | 0 | 61 | 1 | QNCELFEQLGEYK | Yes | |
| 29 | 581.6665 | 1741.8867 | 0 | 17 | 1 | HPYFYAPELLFFAK | Yes | |
| 30 | 955.9536 | 1909.9243 | 0 | 26 | 1 | RPCFSALEVDETYVPK | Yes | |

TABLE 3-continued

| ALBU_HUMAN P02768 | Mass: | 71317 | Total score: | 1337 | Peptides matched: Serum albumin precursor | 37 | |
|---|---|---|---|---|---|---|---|
| Pept No | Observed | Mr(calc) | Missed cleavage | Score | Rank Peptide | Accept or not | Comments |
| 31 | 955.95 | 1909.9243 | 0 | 20 | 1 RPCFSALEVDETYVPK | No | Same parent ion as pept 30 |
| 32 | 1023.0412 | 2044.088 | 0 | 39 | 1 VFDEFKPLVEEPQNLIK | Yes | |
| 33 | 696.2625 | 2085.8302 | 0 | 35 | 1 VHTECCHGDLLECADDR | Yes | |
| 34 | 1043.9149 | 2085.8302 | 0 | 60 | 1 VHTECCHGDLLECADDR | Yes | Same sequence as Pept33, but different charge |
| 35 | 522.4952 | 2085.8302 | 0 | 35 | 1 VHTECCHGDLLECADDR | Yes | Same sequence as Pept33-34, but different charge |
| 36 | 862.3713 | 2584.1104 | 1 | 18 | 1 VHTECCHGDLLECAD DRADLAK | Yes | Overlapped sequence with pept 35, but different parent ion |
| 37 | 884.0808 | 2649.2566 | 0 | 34 | 1 LVRPEVDVMCTAFHD NEETFLK | Yes | |

Observed unique parent ions 33

(4) Counting of the Number of Observable Peptides Per Protein

As explained above in FIG. 4, this calculation was performed according to the below Steps 1 to 6;

Step 1 (see S121 in FIG. 4): Determination of the mass range using observed peptides and the scan range of mass spec. This step was carried out by using the actual observed mass spectrometry of the peptides, i.e., the observed peptides and the scan range of the mass spec.

Step 2 (see S122 in FIG. 4): Calculation of the predicted retention times in each observed peptides, based on Meek's equation; As explained in S122 in FIG. 4, since it is appreciated that amino acid sequences of each observed peptides can generally be determined by the MS/MS method, retention time of the observed peptides could be calculated according to the Meek's equation in which there is the relationship between the known amino acid sequence and the retention time.

Step 3 (see S123 in FIG. 4): Determination of the retention time range using observed peptides; Similarly, this step was carried out by use of the Meek's equation.

Step 4 (see S124 in FIG. 4): Calculation of the digested tryptic peptides without missed cleavage in silico; As described in S124 of FIG. 4, molecular weight (MW) and the predicted retention time of the digested tryptic peptides could be calculated from amino acid sequences of the digested tryptic peptides, which was determined in silico.

Step 5 (see S125 in FIG. 4): The observable peptides were sorted according to MW and the predicted retention time by use of results of S124.

Step 6 (see S126 in FIG. 4): The number of the observable peptides per protein was counted, on the basis that MW and the predicted retention time of the observable peptides fall both within the mass range (Step 121) and the retention time range (Step 123).

According to results using the sample in Table 2, mass range and retention time range were determined as in Table 4.

TABLE 4

Mass range: 700-2800
Retention time range: 40-150

| Pept No | Peptide Mass | Retention time | Peptide | Accept or not |
|---|---|---|---|---|
| 1 | 277.14603 | 35.47 | MK | No |
| 2 | 2036.0772 | 166.9 | WVTFISLLFLFSSAYSR | No |
| 3 | 477.27 | 49.91 | GVFR | No |
| 4 | 174.11169 | 27.66 | R | No |
| 5 | 469.22852 | 20.51 | DAHK | No |
| 6 | 697.35077 | 29.75 | SEVAHR | No |
| 7 | 293.17396 | 42.12 | FK | No |
| 8 | 950.43458 | 61.1 | DLGEENFK | Yes |
| 9 | 2432.2563 | 130.71 | ALVLIAFAQYLQQCPFEDHVK | Yes |
| 10 | 1148.6078 | 77.64 | LVNEVTEFAK | Yes |
| 11 | 1383.5283 | 43.9 | TCVADESAENCDK | Yes |
| 12 | 1016.5291 | 64.57 | SLHTLFGDK | Yes |
| 13 | 875.48992 | 67.93 | LCTVATLR | Yes |
| 14 | 1319.4833 | 52.14 | ETYGEMADCCAK | Yes |
| 15 | 657.30824 | 31.51 | QEPER | No |
| 16 | 1017.4702 | 45.5 | NECFLQHK | Yes |
| 17 | 939.44106 | 43.21 | DDNPNLPR | Yes |
| 18 | 2592.2354 | 110.88 | LVRPEVDVMCTAFHDNEETFLK | Yes |
| 19 | 146.10554 | 26.54 | K | No |
| 20 | 926.48621 | 72.63 | YLYEIAR | Yes |
| 21 | 174.11169 | 27.66 | R | No |
| 22 | 1741.8869 | 114.7 | HPYFYAPELLFFAK | Yes |
| 23 | 174.11169 | 27.66 | R | No |
| 24 | 309.16887 | 33.88 | YK | No |
| 25 | 1256.5166 | 52.52 | AAFTECCQAADK | Yes |
| 26 | 714.40988 | 59.32 | AACLLPK | Yes |

TABLE 4-continued

Mass range: 700-2800
Retention time range: 40-150

| Pept No | Peptide Mass | Retention time | Peptide | Accept or not |
|---|---|---|---|---|
| 27 | 644.34938 | 61.04 | LDELR | No |
| 28 | 447.19656 | 30.1 | DEGK | No |
| 29 | 462.24384 | 31.3 | ASSAK | No |
| 30 | 302.17027 | 26.46 | QR | No |
| 31 | 259.18961 | 41.21 | LK | No |
| 32 | 648.32653 | 41.34 | CASLQK | No |
| 33 | 507.24418 | 45.11 | FGER | No |
| 34 | 364.21108 | 44.19 | AFK | No |
| 35 | 672.37079 | 59.13 | AWAVAR | No |
| 36 | 502.28637 | 41.44 | LSQR | No |
| 37 | 390.22673 | 42.47 | FPK | No |
| 38 | 879.43385 | 58.42 | AEFAEVSK | Yes |
| 39 | 788.46441 | 67.48 | LVTDLTK | Yes |
| 40 | 1914.766 | 54.16 | VHTECCHGDLLECADDR | Yes |
| 41 | 516.2908 | 47.04 | ADLAK | No |
| 42 | 1385.6133 | 57.4 | YICENQDSISSK | Yes |
| 43 | 259.18961 | 41.21 | LK | No |
| 44 | 1190.5676 | 50.35 | ECCEKPLLEK | Yes |
| 45 | 2916.3159 | 117.83 | SHCIAEVENDEMPADLPSLAADFVESK | No |
| 46 | 463.2101 | 34.33 | DVCK | No |
| 47 | 694.32864 | 38.77 | NYAEAK | No |
| 48 | 1622.7804 | 124.55 | DVFLGMFLYEYAR | Yes |
| 49 | 174.11169 | 27.66 | R | No |
| 50 | 1310.7347 | 85.87 | HPDYSVVLLLR | Yes |
| 51 | 330.22673 | 43.28 | LAK | No |
| 52 | 983.48118 | 57.39 | TYETTLEK | Yes |
| 53 | 1380.5261 | 33.61 | CCAAADPHECYAK | No |
| 54 | 2044.0882 | 108.35 | VFDEFKPLVEEPQNLIK | Yes |
| 55 | 1599.724 | 80.32 | QNCELFEQLGEYK | Yes |
| 56 | 959.5553 | 79 | FQNALLVR | Yes |
| 57 | 410.21655 | 35.26 | YTK | No |
| 58 | 146.10554 | 26.54 | K | No |
| 59 | 1510.8356 | 76.16 | VPQVSTPTLVEVSR | Yes |
| 60 | 430.25401 | 39.13 | NLGK | No |
| 61 | 389.22746 | 33.52 | VGSK | No |
| 62 | 352.12392 | 24.44 | CCK | No |
| 63 | 580.29694 | 21.52 | HPEAK | No |
| 64 | 174.11169 | 27.66 | R | No |
| 65 | 2403.1638 | 117.37 | MPCAEDYLSVVLNQLCVLHEK | Yes |
| 66 | 673.33954 | 38.54 | TPVSDR | No |
| 67 | 346.22164 | 35.07 | VTK | No |
| 68 | 1023.4478 | 49.82 | CCTESLVNR | Yes |
| 69 | 1852.903 | 78.52 | RPCFSALEVDETYVPK | Yes |
| 70 | 2201.994 | 104.04 | EFNAETFTFHADICTLSEK | Yes |
| 71 | 303.15429 | 30.01 | ER | No |
| 72 | 387.24819 | 36.54 | QIK | No |
| 73 | 146.10554 | 26.54 | K | No |
| 74 | 999.5965 | 74.78 | QTALVELVK | Yes |
| 75 | 508.31219 | 6.27 | HKPK | No |
| 76 | 318.19034 | 29.99 | ATK | No |
| 77 | 516.29079 | 42.36 | EQLK | No |
| 78 | 1341.6276 | 92.87 | AVMDDFAAFVEK | Yes |
| 79 | 352.12392 | 24.44 | CCK | No |
| 80 | 447.19656 | 31.99 | ADDK | No |
| 81 | 1012.4172 | 51.09 | ETCFAEEGK | Yes |
| 82 | 146.10554 | 26.54 | K | No |
| 83 | 1012.5918 | 95.44 | LVAASQAALGL | Yes |

Number of observable peptides 34

The results of the above counting are tabulated in Table 4. In the column of "Accept or not" in Table 2, based on the results of calculation of the observable peptides in silico, the term "Yes" refers to the observable peptides falling both within the mass range and the retention time range and the term "No" means that the observable peptides falling outside either the mass range or the retention time range.

(5) Calculation of EMPAI Value Using (3) and (4)

According to the above equations (1) and (2), EMPAI was calculated by using results of the above (3) and (4). The results of EMPAI are tabulated in Table 5. As can be seen in Table 5, a value of EMPAI using the sample in Table 2 was 8.345.

TABLE 5

| | | |
|---|---|---|
| Number of observed unique parent ions | 33 | |
| Number of observable peptides | 34 | |
| EMPAI | 8.345 | $EMPAI = 10^{PAI} - 1$ |

Absolute Quantitation Using EMPAI

Figure 8:
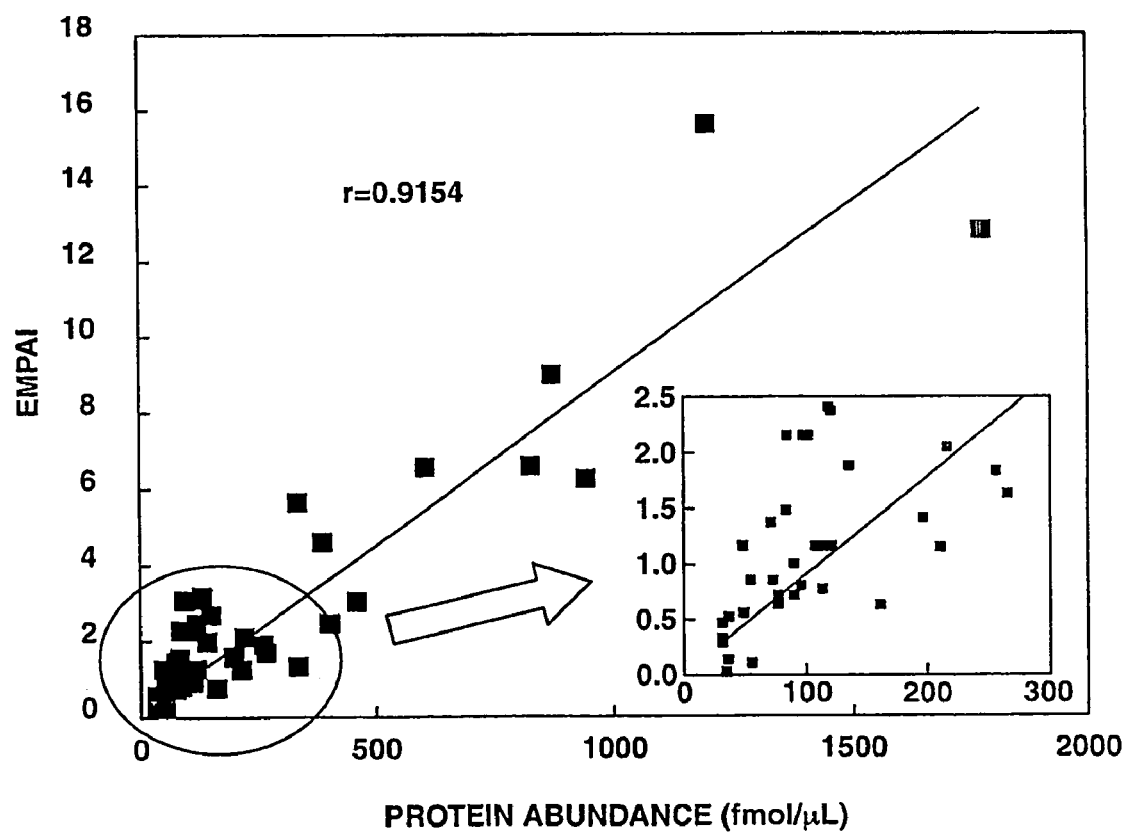
FIG. 8 shows the relationship between protein concentrations and EMPAI for 47 proteins in neuro2a cells.
Figure 9:
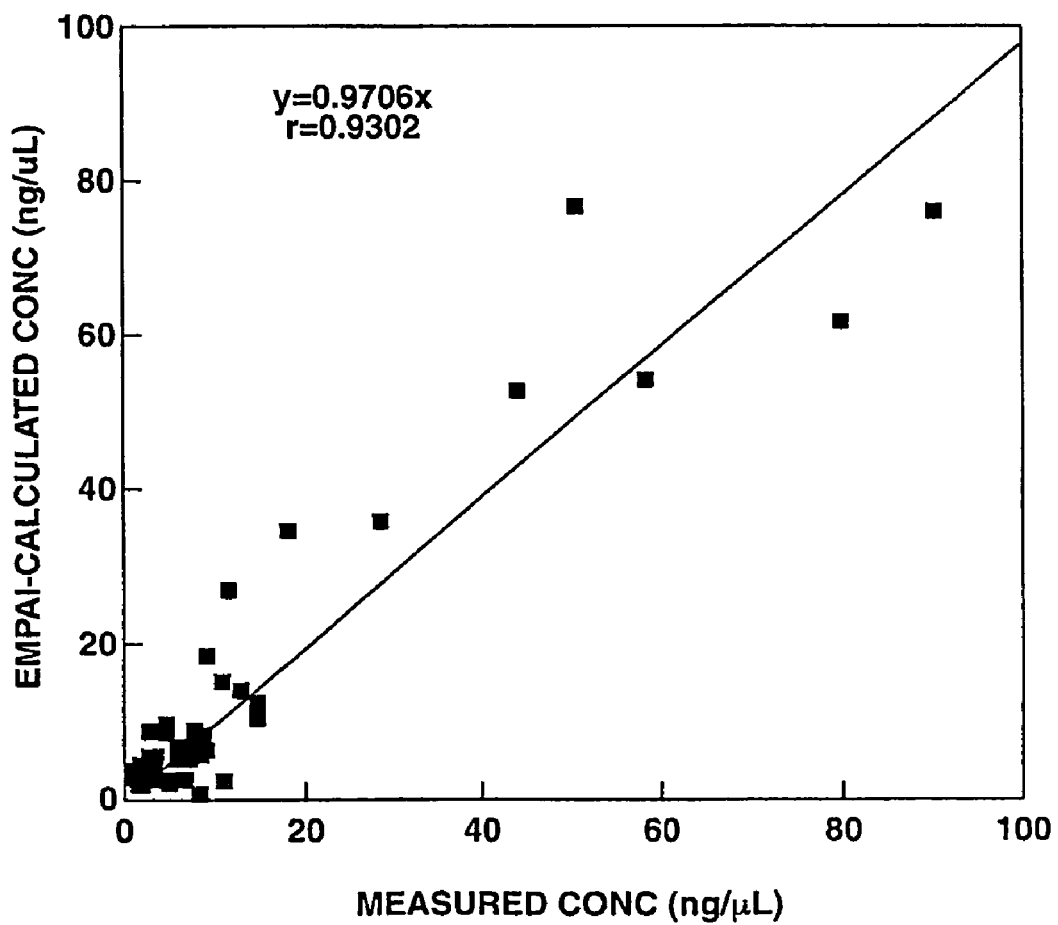
FIG. 9 shows the results of absolute quantitation of 47 proteins in neuro2a using EMPAI according to the present invention.

Although PAI can estimate the abundance relationship between proteins, it cannot express the molar fraction directly. Therefore, the present inventor derived a new parameter, EMPAI, from PAI, as described in Protein Abundance Determination section as the equation (2), which is directly proportional to protein contents as shown in FIG. 8. In order to calculate the absolute concentrations, total protein amounts were measured in weight by BCA assay and the weight fractions of 47 proteins among 336 neuro2a proteins were calculated using equation (4): As shown in FIG. 9, the EMPAI-based concentrations were highly consistent with the actual values (y=0.97x, r=0.93) to and the deviation percentage to the actual values ranged from 3% to 260%, and the average was 63%. Because the present inventor used BCA assay for total protein amounts, these values were easily changed. Nevertheless, this EMPAI approach provides quite accurate index for comprehensive absolute quantitation.

Application to Comprehensive Protein Expression Analysis

Figure 10:
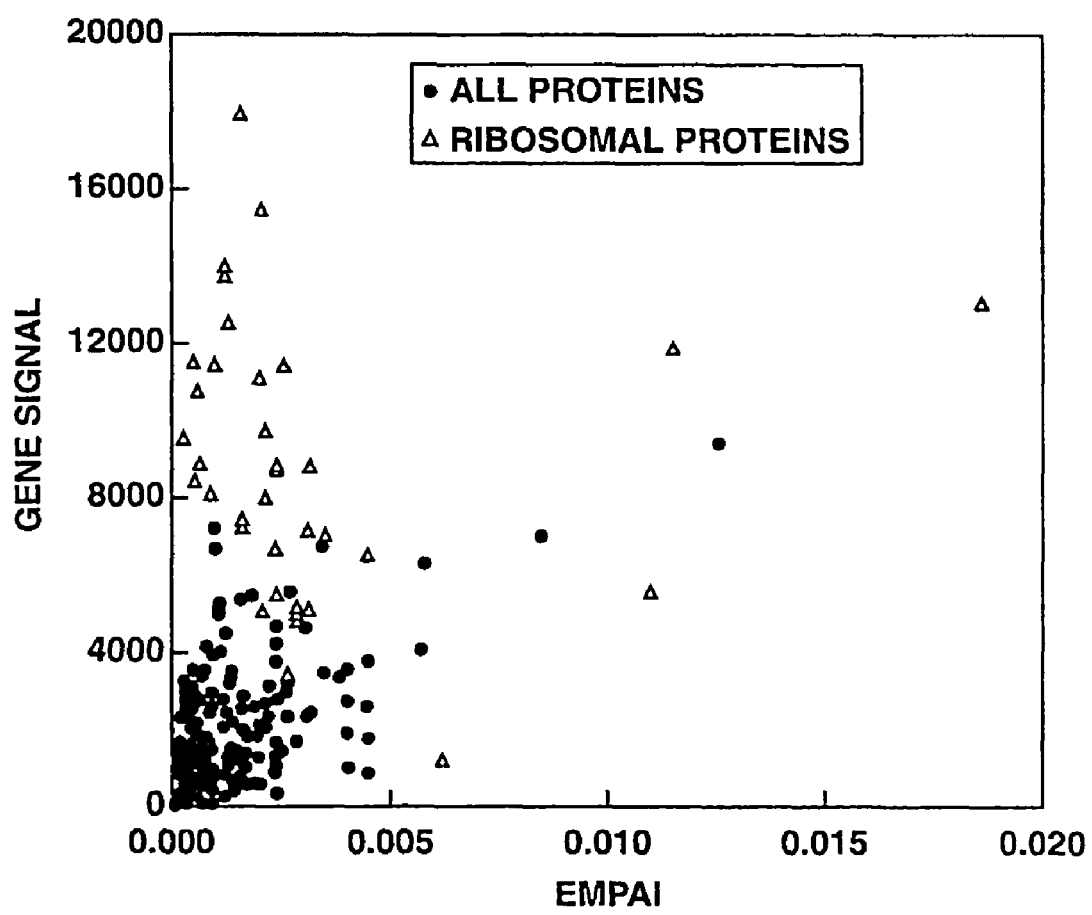
FIG. 10 shows the comparison between gene and protein expression in HCT116 cells according to one embodiment of the present invention.

PAI is really convenient to produce protein expression data from just single LCMSMS run. The present inventor applies this approach to compare it to gene expression in HCT116 human cancer cells. DNA microarray provided expression data of 4971 genes, whereas single LCMS run provided 402 identified proteins based on 1811 peptides with unique sequences. Bridging gene symbols with protein accession numbers resulted in total 227 genes/proteins employed for the expression comparison study. As expected, slight correlation was observed as expected from previous studies on yeast [18,26]. Interestingly, most of outliers were ribosomal proteins (see FIG. 10). It is well known that unlike prokaryotes such as *E. coli*, mammalian cells regulate the expression levels of ribosomal proteins not only by transcription, but also transport of mRNA, translation, and the degradation of excess amounts of proteins unassociated with rRNA [27,28]. The present inventor also did comparison study between gene and protein expression using EMPAI for *E. coli* and did not find such a deviation of ribosomal proteins. Although both gene and protein expression data are not so accurate as to discriminate 10% difference for instance, it is quite helpful to obtain the brief overview as shown above.

INDUSTRIAL APPLICABILITY

According to the present invention, it is established the scale for absolute protein abundance named EMPAI. Because EMPAI is easily calculated from the output information of database search engines such as Mascot, it is possible to apply this approach to the previously measured or published dataset to add the quantitative information without any additional step. EMPAI can also use for relative quantitation, especially in the cases where isotope-based approaches cannot be applied because of quantitative changes that are too large for accurate measurements of ratios, because metabolic labelling is not possible or because sensitivity constraints do not allow chemical labelling techniques. In such cases, EMPAI values of proteins in one sample can compare to those in another sample, and the outliers from the EMPAI correlation between two samples can be determined as increasing or decreasing proteins.

This EMPAI approach can also apply to multidimensional separation-MSMS to extend the coverage of proteins. Further improvement would be possible to consider MS instrument-dependent parameters such as ionization dependence on m/z region. Since the EMPAI index can be calculated with a simple script and does not require further experimentation in protein identification experiments, we suggest its routine use in the reporting of proteomic results.

REFERENCES

The following references cited herein are hereby incorporated by reference in their entirety.

[1] R. Aebersold, M. Mann, Nature 422 (2003) 198.
[0] Y. Oda, K. Huang, F. R. Cross, D. Cowburn, B. T. Chait, Proc Natl Acad Sci U S A 96 (1999) 6591.
[3] S. P. Gygi, B. Rist, S. A. Gerber, F. Turecek, M. H. Gelb, R. Aebersold, Nat Biotechnol 17 (1999) 994.
[4] S. E. Ong, B. Blagoev, I. Kratchmarova, D. B. Kristensen, H. Steen, A. Pandey, M. Mann, Mol Cell Proteomics 1 (2002) 376.
[5] M. J. MacCoss, C. C. Wu, H. Liu, R. Sadygov, J. R. Yates, 3rd, Anal Chem 75 (2003) 6912.
[6] L. J. Foster, C. L. De Hoog, M. Mann, Proc Natl Acad Sci USA 100 (2003) 5813.
[7] B. Blagoev, I. Kratchmarova, S. E. Ong, M. Nielsen, L. J. Foster, M. Mann, Nat Biotechnol 21 (2003) 315.
[8] J. A. Ranish, E. C. Yi, D. M. Leslie, S. O. Purvine, D. R. Goodlett, J. Eng, R. Aebersold, Nat Genet 33 (2003) 349.
[9] W. X. Schulze, M. Mann, J Biol Chem 279 (2004) 10756.
[10] Y. Oda, T. Owa, T. Sato, B. Boucher, S. Daniels, H. Yamanaka, Y. Shinohara, A. Yokoi, J. Kuromitsu, T. Nagasu, Anal Chem 75 (2003) 2159.
[11] J. R. Barr, V. L. Maggio, D. G. Patterson, Jr., G. R. Cooper, L. O. Henderson, W. E. Turner, S. J. Smith, W. H. Hannon, L. L. Needham, E. J. Sampson, Clin Chem 42 (1996) 1676.
[12] S. A. Gerber, J. Rush, O. Stemman, M. W. Kirschner, S. P. Gygi, Proc Natl Acad Sci USA 100 (2003) 6940.
[13] J. Havlis, A. Shevchenko, Anal Chem 76 (2004) 3029.
[14] R. W. Corbin, O. Paliy, F. Yang, J. Shabanowitz, M. Platt, C. E. Lyons, Jr., K. Root, J. McAuliffe, M. I. Jordan, S. Kustu, E. Soupene, D. F. Hunt, Proc Natl Acad Sci USA 100 (2003) 9232.
[15] E. Lasonder, Y. Ishihama, J. S. Andersen, A. M. Vermunt, A. Pain, R. W. Sauerwein, W. M. Eling, N. Hall, A. P. Waters, H. G. Stunnenberg, M. Mann, Nature 419 (2002) 537.
[16] Y. Shen, R. Zhao, S. J. Berger, G. A. Anderson, N. Rodriguez, R. D. Smith, Anal Chem 74 (2002) 4235.
[17] J. Rappsilber, U. Ryder, A. I. Lamond, M. Mann, Genome Res 12 (2002) 1231.
[18] H. Liu, R. G. Sadygov, J. R. Yates, Anal Chem (2004) 76, 4193-4201.
[19] J. Rappsilber, Y. Ishihama, G. Mittler, P. Mortensen, L. Foster, M. Mann, in Proceedings of 51st ASMS Conference on Mass Spectrometry, Montreal, Canada, 2003.
[20] J. S. Andersen, C. J. Wilkinson, T. Mayor, P. Mortensen, E. A. Nigg, M. Mann, Nature 426 (2003) 570.
[21] J. Rappsilber, Y. Ishihama, M. Mann, Anal Chem 75 (2003) 663.
[22] Y. Ishihama, J. Rappsilber, J. S. Andersen, M. Mann, J Chromatogr A 979 (2002) 233.
[23] J. L. Meek, Proc Natl Acad Sci USA 77 (1980) 1632.
[24] Y. Sakamoto, N. Kawakami, T. Sasagawa, J Chromatogr 442 (1988) 69.
[25] A. J. Link, J. Eng, D. M. Schieltz, E. Carmack, G. J. Mize, D. R. Morris, B. M. Garvik, J. R. Yates, 3rd, Nat Biotechnol 17 (1999) 676.
[26] S. P. Gygi, Y. Rochon, B. R. Franza, R. Aebersold, Mol Cell Biol 19 (1999) 1720.
[27] K. Tsurugi, Seikagaku 61 (1989) 271.
[28] W. H. Mager, Biochem Biophys Acta 949 (1988) 1.

What is claimed is:

1. A method for executing quantitation of protein content in a sample of biological material, said method comprising the steps of:
   (a) identifying by mass spectrometry one or more proteins to be quantified;
   (b) measuring by LC-MS/MS a number of observed peptides per protein ($N_{obsd}$) from an enzymatic digestion of each protein;
   (c) calculating a number of observable peptides per protein ($N_{obsbl}$) from in silico modeling of the enzymatic digestion of each protein; and
   (d) computing the following equation to obtain an exponentially modified Protein Abundance Index (EMPAI) of each protein $EMPAI = 10^{N_{obsd}/N_{obsbl}} - 1$;

(e) calculating protein contents based on $$\text{protein contents (mol \%)} = \frac{EMPAI}{\sum (EMPAI)} \times 100, \text{ or}$$

$$\text{protein contents (weight \%)} = \frac{EMPAI \times MW}{\sum (EMPAI \times MW)} \times 100,$$

wherein $\Sigma(EMPAI)$ is the summation of EMPAI values for all identified protein or proteins and MW represents molecular weight of each protein identified.

2. A computer program product for executing quantitation of protein content in a sample of biological material, said program product comprising: a computer readable storage medium having a computer program stored there on for performing the steps:
   (a) identifying by mass spectrometry one or more proteins to be quantified;
   (b) measuring by LC-MS/MS a number of observed peptides per protein ($N_{obsd}$) from an enzymatic digestion of each protein;
   (c) calculating a number of observable peptides per protein ($N_{obsbl}$) from in silico modeling of the enzymatic digestion of each protein; and
   (d) computing the following equation to obtain an exponentially modified Protein Abundance Index (EMPAI) of each protein $EMPAI = 10^{N_{obsd}/N_{obsbl}} - 1$;

(e) calculating protein contents based on $$\text{protein contents (mol \%)} = \frac{EMPAI}{\sum (EMPAI)} \times 100, \text{ or}$$

$$\text{protein contents (weight \%)} = \frac{EMPAI \times MW}{\sum (EMPAI \times MW)} \times 100,$$

wherein $\Sigma(EMPAI)$ is the summation of EMPAI values for all identified protein or proteins and MW represents molecular weight of each protein identified.

3. The computer program product according to claim 2, wherein the product is a computer readable recording medium which can be read by a computer.

4. An analytical apparatus for executing quantitation of protein content in a sample of biological material, comprising:
   identifying means for receiving information as to mass spectrometric data of one or more proteins obtained by LC-MS/MS and identifying by mass spectrometry such one or more proteins to be quantified;
   measuring means for measuring by LC-MS/MS a number of observed peptides per protein ($N_{obsd}$) from an enzymatic digestion of each protein;
   calculating means for calculating a number of observable peptides per protein ($N_{obsbl}$) from in silico modeling of the enzymatic digestion of each protein; and
   computing means for computing following equation to obtain an exponentially modified Protein Abundance Index (EMPAI) of each protein $EMPAI = 10^{N_{obsd}/N_{obsbl}} - 1$;

computing means for computing protein contents based on $$\text{protein contents (mol \%)} = \frac{EMPAI}{\sum (EMPAI)} \times 100, \text{ or}$$

$$\text{protein contents (weight \%)} = \frac{EMPAI \times MW}{\sum (EMPAI \times MW)} \times 100,$$

wherein $\Sigma(EMPAI)$ is the summation of EMPAI values for all identified protein or proteins and MW represents molecular weight of each protein identified.

* * * * *